US009922170B2

(12) United States Patent
Trosien et al.

(10) Patent No.: US 9,922,170 B2
(45) Date of Patent: Mar. 20, 2018

(54) TREATMENT ANALYSIS SYSTEMS AND METHODS

(71) Applicant: Align Technology, Inc., San Jose, CA (US)

(72) Inventors: Andrew Trosien, San Francisco, CA (US); Eric Kuo, San Francisco, CA (US); Ross Miller, Sunnyvale, CA (US)

(73) Assignee: Align Technology, Inc., San Jose, CA (US)

(*) Notice: Subject to any disclaimer, the term of this patent is extended or adjusted under 35 U.S.C. 154(b) by 697 days.

(21) Appl. No.: 14/511,119

(22) Filed: Oct. 9, 2014

(65) Prior Publication Data

US 2015/0025907 A1   Jan. 22, 2015

Related U.S. Application Data

(63) Continuation of application No. 12/539,553, filed on Aug. 11, 2009, now Pat. No. 8,930,219, which is a continuation of application No. 09/557,382, filed on Apr. 25, 2000, now abandoned.

(51) Int. Cl.
| | |
|---|---|
| *G06Q 10/00* | (2012.01) |
| *G06F 19/00* | (2018.01) |
| *G06Q 10/10* | (2012.01) |
| *G06Q 50/24* | (2012.01) |
| *A61C 7/00* | (2006.01) |

(52) U.S. Cl.
CPC ........ *G06F 19/345* (2013.01); *G06F 19/3443* (2013.01); *G06Q 10/10* (2013.01); *G06Q 50/24* (2013.01); *A61C 7/002* (2013.01)

(58) Field of Classification Search
CPC ...... G06Q 50/22; G06Q 50/24; G06F 19/322; G06F 19/323–19/327; A61C 7/00; A61C 7/08; A61C 7/146; A61C 5/00
USPC ........ 705/2, 3; 433/2, 3, 6, 18, 24, 215, 229
See application file for complete search history.

(56) References Cited

U.S. PATENT DOCUMENTS

| | | | |
|---|---|---|---|
| 2,467,432 | A | 4/1949 | Kesling |
| 3,407,500 | A | 10/1968 | Kesling |
| 3,600,808 | A | 8/1971 | Reeve |
| 3,660,900 | A | 5/1972 | Andrews |
| 3,683,502 | A | 8/1972 | Wallshein |
| 3,738,005 | A | 6/1973 | Cohen |
| 3,860,803 | A | 1/1975 | Levine |

(Continued)

FOREIGN PATENT DOCUMENTS

| | | |
|---|---|---|
| AU | 3031677 A | 5/1979 |
| CA | 1121955 | 4/1982 |

(Continued)

OTHER PUBLICATIONS

AADR. American Association for Dental Research, Summary of Activities, Mar. 20-23, 1980, Los ngeles, CA, p. 195.

(Continued)

*Primary Examiner* — Jonathan Ng
*Assistant Examiner* — Jason S Tiedeman
(74) *Attorney, Agent, or Firm* — Wilson Sonsini Goodrich & Rosati

(57) ABSTRACT

A dental treatment planning system includes an input form to receive one or more dental patient inputs; and an engine adapted to receive the dental patient data from the input form and validating the dental patient data in a predetermined sequence.

14 Claims, 10 Drawing Sheets

(56) References Cited

U.S. PATENT DOCUMENTS

| | | | |
|---|---|---|---|
| 3,916,526 A | 11/1975 | Schudy | |
| 3,922,786 A | 12/1975 | Lavin | |
| 3,950,851 A | 4/1976 | Bergersen | |
| 3,983,628 A | 10/1976 | Acevedo | |
| 4,014,096 A | 3/1977 | Dellinger | |
| 4,195,046 A | 3/1980 | Kesling | |
| 4,253,828 A | 3/1981 | Coles et al. | |
| 4,324,546 A | 4/1982 | Heitlinger et al. | |
| 4,324,547 A | 4/1982 | Arcan et al. | |
| 4,348,178 A | 9/1982 | Kurz | |
| 4,478,580 A | 10/1984 | Barrut | |
| 4,500,294 A | 2/1985 | Lewis | |
| 4,504,225 A | 3/1985 | Yoshii | |
| 4,505,673 A | 3/1985 | Yoshii | |
| 4,526,540 A | 7/1985 | Dellinger | |
| 4,575,330 A | 3/1986 | Hull | |
| 4,575,805 A | 3/1986 | Moermann | |
| 4,591,341 A | 5/1986 | Andrews | |
| 4,609,349 A | 9/1986 | Cain | |
| 4,610,629 A * | 9/1986 | Schrems | A61C 19/04 433/213 |
| 4,611,288 A | 9/1986 | Duret et al. | |
| 4,656,860 A | 4/1987 | Orthuber et al. | |
| 4,663,720 A | 5/1987 | Duret et al. | |
| 4,664,626 A | 5/1987 | Kesling | |
| 4,676,747 A | 6/1987 | Kesling | |
| 4,742,464 A | 5/1988 | Duret et al. | |
| 4,755,139 A | 7/1988 | Abbatte et al. | |
| 4,763,791 A | 8/1988 | Halverson et al. | |
| 4,793,803 A | 12/1988 | Martz | |
| 4,798,534 A | 1/1989 | Breads | |
| 4,836,778 A | 6/1989 | Baumrind et al. | |
| 4,837,732 A | 6/1989 | Brandestini et al. | |
| 4,850,864 A | 7/1989 | Diamond | |
| 4,850,865 A | 7/1989 | Napolitano | |
| 4,856,991 A | 8/1989 | Breads et al. | |
| 4,877,398 A | 10/1989 | Kesling | |
| 4,880,380 A | 11/1989 | Martz | |
| 4,889,238 A | 12/1989 | Batchelor | |
| 4,890,608 A | 1/1990 | Steer | |
| 4,935,635 A | 6/1990 | O'Harra | |
| 4,936,862 A | 6/1990 | Walker et al. | |
| 4,937,928 A | 7/1990 | van der Zel | |
| 4,941,826 A | 7/1990 | Loran et al. | |
| 4,964,770 A | 10/1990 | Steinbichler et al. | |
| 4,975,052 A | 12/1990 | Spencer et al. | |
| 4,983,334 A | 1/1991 | Adell | |
| 5,011,405 A * | 4/1991 | Lemchen | A61C 13/0003 433/229 |
| 5,017,133 A | 5/1991 | Miura | |
| 5,027,281 A | 6/1991 | Rekow et al. | |
| 5,035,613 A | 7/1991 | Breads et al. | |
| 5,055,039 A | 10/1991 | Abbatte et al. | |
| 5,059,118 A | 10/1991 | Breads et al. | |
| 5,100,316 A | 3/1992 | Wildman | |
| 5,121,333 A | 6/1992 | Riley et al. | |
| 5,125,832 A | 6/1992 | Kesling | |
| 5,128,870 A | 7/1992 | Erdman et al. | |
| 5,130,064 A | 7/1992 | Smalley | |
| 5,131,843 A | 7/1992 | Hilgers et al. | |
| 5,131,844 A | 7/1992 | Marinaccio et al. | |
| 5,139,419 A | 8/1992 | Andreiko et al. | |
| 5,145,364 A | 9/1992 | Martz et al. | |
| 5,176,517 A | 1/1993 | Truax | |
| 5,184,306 A | 2/1993 | Erdman et al. | |
| 5,186,623 A | 2/1993 | Breads et al. | |
| 5,257,203 A | 10/1993 | Riley et al. | |
| 5,273,429 A | 12/1993 | Rekow et al. | |
| 5,278,756 A | 1/1994 | Lemchen et al. | |
| 5,328,362 A | 7/1994 | Watson et al. | |
| 5,338,198 A | 8/1994 | Wu et al. | |
| 5,340,309 A | 8/1994 | Robertson | |
| 5,342,202 A | 8/1994 | Deshayes | |
| 5,368,478 A | 11/1994 | Andreiko et al. | |
| 5,382,164 A | 1/1995 | Stern | |
| 5,395,238 A | 3/1995 | Andreiko et al. | |
| 5,440,326 A | 8/1995 | Quinn | |
| 5,440,496 A | 8/1995 | Andersson et al. | |
| 5,447,432 A | 9/1995 | Andreiko et al. | |
| 5,452,219 A | 9/1995 | Dehoff et al. | |
| 5,454,717 A | 10/1995 | Andreiko et al. | |
| 5,456,600 A | 10/1995 | Andreiko et al. | |
| 5,431,562 A | 11/1995 | Andreiko et al. | |
| 5,474,448 A | 12/1995 | Andreiko et al. | |
| 5,475,585 A * | 12/1995 | Bush | G06Q 20/02 235/380 |
| RE35,169 E | 3/1996 | Lemchen et al. | |
| 5,518,397 A | 5/1996 | Andreiko et al. | |
| 5,528,735 A | 6/1996 | Strasnick et al. | |
| 5,533,895 A | 7/1996 | Andreiko et al. | |
| 5,542,842 A | 8/1996 | Andreiko et al. | |
| 5,549,476 A | 8/1996 | Stern | |
| 5,562,448 A | 10/1996 | Mushabac | |
| 5,587,912 A | 12/1996 | Andersson et al. | |
| 5,605,459 A | 2/1997 | Kuroda et al. | |
| 5,607,305 A | 3/1997 | Andersson et al. | |
| 5,614,075 A | 3/1997 | Andre | |
| 5,621,648 A | 4/1997 | Crump | |
| 5,645,420 A | 7/1997 | Bergersen | |
| 5,645,421 A | 7/1997 | Slootsky | |
| 5,655,653 A | 8/1997 | Chester | |
| 5,683,243 A | 11/1997 | Andreiko et al. | |
| 5,692,894 A | 12/1997 | Schwartz et al. | |
| 5,724,968 A * | 3/1998 | Iliff | G06F 19/322 600/300 |
| 5,725,376 A | 3/1998 | Poirier | |
| 5,725,378 A | 3/1998 | Wang | |
| 5,733,126 A | 3/1998 | Andersson et al. | |
| 5,740,267 A | 4/1998 | Echerer et al. | |
| 5,742,700 A | 4/1998 | Yoon et al. | |
| 5,799,100 A | 8/1998 | Clarke et al. | |
| 5,800,174 A | 9/1998 | Andersson | |
| 5,823,778 A | 10/1998 | Schmitt et al. | |
| 5,848,115 A | 12/1998 | Little et al. | |
| 5,857,853 A | 1/1999 | van Nifterick et al. | |
| 5,866,058 A | 2/1999 | Batchelder et al. | |
| 5,879,158 A * | 3/1999 | Doyle | A61C 7/146 433/24 |
| 5,880,961 A | 3/1999 | Crump | |
| 5,880,962 A | 3/1999 | Andersson et al. | |
| 5,882,192 A * | 3/1999 | Bergersen | A61C 7/00 433/2 |
| 5,882,912 A | 3/1999 | Bergersen | |
| 5,934,288 A | 8/1999 | Avila et al. | |
| 5,957,686 A | 9/1999 | Anthony | |
| 5,964,587 A | 10/1999 | Sato | |
| 5,971,754 A | 10/1999 | Sondhi et al. | |
| 5,975,893 A | 11/1999 | Chishti et al. | |
| 5,980,246 A * | 11/1999 | Ramsay | A61C 7/06 433/5 |
| 6,004,276 A * | 12/1999 | Wright | G06F 19/322 128/923 |
| 6,015,289 A | 1/2000 | Andreiko et al. | |
| 6,044,309 A | 3/2000 | Honda | |
| 6,049,743 A | 4/2000 | Baba | |
| 6,062,861 A | 5/2000 | Andersson | |
| 6,068,482 A | 5/2000 | Snow | |
| 6,099,314 A | 8/2000 | Kopelman et al. | |
| 6,123,544 A | 9/2000 | Cleary | |
| 6,152,731 A | 11/2000 | Jordon et al. | |
| 6,183,248 B1 | 2/2001 | Chishti et al. | |
| 6,190,165 B1 | 2/2001 | Andreiko et al. | |
| 6,200,278 B1 * | 3/2001 | Arnett | A61C 7/00 600/587 |
| 6,217,325 B1 | 4/2001 | Chishti et al. | |
| 6,217,334 B1 | 4/2001 | Hultgren | |
| 6,227,850 B1 | 5/2001 | Chishti et al. | |
| 6,244,861 B1 | 6/2001 | Andreiko et al. | |
| 6,269,339 B1 * | 7/2001 | Silver | G06F 19/3456 600/300 |
| 6,283,761 B1 * | 9/2001 | Joao | G06F 19/322 128/923 |
| 6,309,215 B1 | 10/2001 | Phan et al. | |

(56) References Cited

U.S. PATENT DOCUMENTS

| | | | |
|---|---|---|---|
| 6,315,553 B1 | 11/2001 | Sachdeva et al. | |
| 6,322,359 B1 | 11/2001 | Jordan et al. | |
| 6,350,120 B1 | 2/2002 | Sachdeva et al. | |
| 6,382,975 B1 | 5/2002 | Poirier | |
| 6,398,548 B1 | 6/2002 | Muhammad et al. | |
| 6,402,707 B1 | 6/2002 | Ernst | |
| 6,431,870 B1* | 8/2002 | Sachdeva | A61C 7/00 433/213 |
| 6,463,344 B1 | 10/2002 | Pavlovskaia et al. | |
| 6,471,511 B1* | 10/2002 | Chishti | A61C 7/00 433/24 |
| 6,482,298 B1 | 11/2002 | Bhatnagar | |
| 6,524,101 B1 | 2/2003 | Phan et al. | |
| 6,554,611 B2 | 4/2003 | Chishti et al. | |
| 6,572,372 B1 | 6/2003 | Phan et al. | |
| 6,575,751 B1* | 6/2003 | Lehmann | A61C 19/00 433/223 |
| 6,587,828 B1* | 7/2003 | Sachdeva | G06F 19/3437 705/3 |
| 6,629,840 B2 | 10/2003 | Chishti et al. | |
| 6,705,863 B2 | 3/2004 | Phan et al. | |
| 6,722,880 B2 | 4/2004 | Chishti et al. | |
| 6,757,898 B1 | 6/2004 | Ilsen et al. | |
| 6,820,235 B1* | 11/2004 | Bleicher | G06F 19/325 600/300 |
| 8,930,219 B2 | 1/2015 | Troisen et al. | |
| 2002/0004725 A1* | 1/2002 | Martin | G06F 19/3481 705/2 |
| 2002/0006597 A1* | 1/2002 | Andreiko | A61C 7/00 433/24 |
| 2003/0009252 A1 | 1/2003 | Pavlovskaia et al. | |
| 2003/0055679 A1* | 3/2003 | Soll | G06F 19/322 705/2 |
| 2003/0139834 A1 | 7/2003 | Nikolskiy et al. | |
| 2003/0224311 A1 | 12/2003 | Cronauer | |
| 2004/0128010 A1 | 7/2004 | Pavlovskaia et al. | |
| 2005/0055118 A1 | 3/2005 | Nikolskiy et al. | |
| 2010/0036682 A1 | 2/2010 | Troisen et al. | |

FOREIGN PATENT DOCUMENTS

| | | | |
|---|---|---|---|
| DE | 2749802 | 5/1978 | |
| DE | 69327661 T | 7/2000 | |
| EP | 0091876 A1 | 10/1983 | |
| EP | 0299490 A2 | 1/1989 | |
| EP | 0376873 A2 | 7/1990 | |
| EP | 0490848 A2 | 6/1992 | |
| EP | 0541500 A1 | 5/1993 | |
| EP | 0667753 B1 | 8/1995 | |
| EP | 0731673 B1 | 9/1996 | |
| EP | 0774933 B1 | 5/1997 | |
| ES | 463897 A1 | 1/1980 | |
| FR | 2369828 A1 | 6/1978 | |
| FR | 2652256 A1 | 3/1991 | |
| GB | 15500777 | 8/1979 | |
| JP | H0428359 A | 1/1992 | |
| JP | H08508174 A | 9/1996 | |
| WO | WO 90/08512 A1 | 8/1990 | |
| WO | WO 91/04713 A1 | 4/1991 | |
| WO | WO 94/10935 A1 | 5/1994 | |
| WO | WO-9815227 A1 | 4/1998 | |
| WO | WO 98/32394 A1 | 7/1998 | |
| WO | WO 98/44865 A1 | 10/1998 | |
| WO | WO 98/58596 A1 | 12/1998 | |
| WO | WO 9858596 A1 * | 12/1998 | A61C 7/00 |

OTHER PUBLICATIONS

Alcaniz, et aL, "An Advanced System for the Simulation and Planning of Orthodontic Treatments," Karl Heinz Hohne and Ron Kikinis (eds.), Visualization in Biomedical Computing, 4th Intl. Conf., VBC '96, Hamburg, Germany, Sep. 22-25, 1996, Springer-Verlag, pp. 511-520.

Alexander et al., "The DigiGraph Work Station Part 2 Clinical Management," JCO, pp. 402-407 (Jul. 1990).
Altschuler et al., "Analysis of 3-D Data for Comparative 3-D Serial Growth Pattern Studies of Oral-Facial Structures," AADR Abstracts, Program and Abstracts of Papers, 57th General Session, IADR Annual Session, Mar. 29, 1979-Apr. 1, 1979, New Orleans Marriot, Journal of Dental Research, vol. 58, Jan. 1979, Special Issue A, p. 221.
Altschuler et al., "Laser Electro-Optic System for Rapid Three-Dimensional (3D) Topographic Mapping of Surfaces," Optical Engineering, 20(6):953-961 (1981).
Altschuler et al., "Measuring Surfaces Space-Coded by a Laser-Projected Dot Matrix," SPIE Imaging q Applications for Automated Industrial Inspection and Assembly, vol. 182, p. 187-191 (1979).
Altschuler, "3D Mapping of Maxillo-Facial Prosthesis," AADR Abstract #607, 2 pages total, (1980).
Andersson et al., "Clinical Results with Titanium Crowns Fabricated with Machine Duplication and Spark Erosion," Acta. Odontol. Scand., 47:279-286 (1989).
Andrews, The Six Keys to Optimal Occlusion Straight Wire, Chapter 3, pp. 13-24 (1989).
Bartels, et al., An Introduction to Splines for Use in Computer Graphics and Geometric Modeling, Morgan Kaufmann Publishers, pp. 422-425 (1987).
Baumrind et al., "A Stereophotogrammetric System for the Detection of Prosthesis Loosening in Total Hip Arthroplasty," NATO Symposium on Applications of Human Biostereometrics, Jul. 9-13, 1978, SPIE, vol. 166, pp. 112-123.
Baumrind et al., "Mapping the Skull in 3-D," reprinted from J. Calif. Dent. Assoc., 48(2), 11 pages total, (1972 Fall Issue).
Baumrind, "A System for Craniofacial Mapping Through the Integration of Data from Stereo X-Ray Films and Stereo Photographs," an invited paper submitted to the 1975 American Society of Photogram Symposium on Close-Range Photogram Systems, University of Ill., Aug. 26-30, 1975, pp. 142-166.
Baumrind, "Integrated Three-Dimensional Craniofacial Mapping: Background, Principles, and Perspectives," Semin. in Orthod., 7(4):223-232 (Dec. 2001).
Begole et al., "A Computer System for the Analysis of Dental Casts," The Angle Orthod., 51(3):253-259 (Jul. 1981).
Bernard et al., "Computerized Diagnosis in Orthodontics for Epidemiological Studies: A Progress Report," Abstract, J. Dental Res. Special Issue, vol. 67, p. 169, paper presented at International Association for Dental Research 66th General Session, Mar. 9-13, 1988, Montreal, Canada.
Bhatia et al., "A Computer-Aided Design for Orthognathic Surgery," Br. J. Oral Maxillofac. Surg., 22:237-253 (1984).
Biggerstaff et al., "Computerized Analysis of Occlusion in the Postcanine Dentition," Am. J. Orthod., 61(3): 245-254 (Mar. 1972).
Biggerstaff, "Computerized Diagnostic Setups and Simulations," Angle Orthod., 40(1):28-36 (Jan. 1970).
Biostar Opeation & Training Manual. Great Lakes Orthodontics, Ltd. 199 Fire Tower Drive, Tonawanda, New York. 14150-5890, 20 pages total (1990).
Blu, et al., "Linear interpolation revitalized", IEEE Trans. Image Proc., 13(5):710-719 (May 2004).
Bourke, "Coordinate System Transformation," (Jun. 1996), p. 1, retrieved from the Internet Nov. 5, 2004, URL <http://astronomy.swin.edu.au/pbourke/prolection/coords>.
Boyd et al., "Three Dimensional Diagnosis and Orthodontic Treatment of Complex Malocclusions With the Invisalipn Appliance," Semin. Orthod., 7(4):274-293 (Dec. 2001).
Brandestini et al., "Computer Machined Ceramic Inlays: In Vitro Marginal Adaptation," J. Dent. Res. Special Issue, Abstracts, vol. 64, p. 208 (1985).
Brook et al., "An Image Analysis System for the Determination of Tooth Dimensions from Study Casts: IK Comparison with Manual Measurements of Mesio-distal Diameter," J. Dent. Res., 65(3):428-431 (Mar. 1986.
Burstone (interview), "Dr. Charles J. Burstone on The Uses of the Computer in Orthodontic Practice (Part 1)," J. Clin. Orthod., 13(7):442-453 (Jul. 1979).

(56) References Cited

OTHER PUBLICATIONS

Burstone (interview), "Dr. Charles J. Burstone on The Uses of the Computer in Orthodontic Practice (Part 2)," J. Clin. Orthod., 13(8):539-551 (Aug. 1979.
Burstone et al., Precision Adjustment of the Transpalatal Lingual Arch: Computer Arch Form In Predetermination, Am, Journal of Orthodontics, vol. 79, No. 2 (Feb. 1981), pp. 115-133.
Cardinal Industrial Finishes, Powder Coatings information posted at <http://www.cardinalpaint.com> on Aug. 25, 2000, 2 pages.
Carnaghan, "An Alternative to Holograms for the Portrayal of Human Teeth," 4th Int'l. Conf. on Holographic Systems, Components and Applications, Sep. 15, 1993, pp. 228-231.
Chaconas et al., "The DigiGraph Work Station, Part 1, Basic Concepts," JCO, pp. 360-367 (Jun. 1990).
Chafetz et al., "Subsidence of the Femoral Prosthesis, A Stereophotogrammetric Evaluation," Clin. Orthop. Relat. Res., No. 201, pp. 60-67 (Dec. 1985).
Chiappone, (1980). Constructing the Gnathologic Setup and Positioner, J. Clin. Orthod, vol. 14, pp. 121-133.
Cottingham, (1969). Gnathologic Clear Plastic Positioner, Am. J. Orthod, vol. 55, pp. 23-31.
Crawford, "CAD/CAM in the Dental Office: Does It Work?", Canadian Dental Journal, vol. 57, No. 2, pp. 121-123 (Feb. 1991).
Crawford, "Computers in Dentistry: Part 1: CAD/CAM: The Computer Moves Chairside," "Part 2: F. Duret—A Man With A Vision," "Part 3: The Computer Gives New Vision—Literally," "Part 4: Bytes 'N Bites" The Computer Moves From The Front Desk To The Operatory, Canadian Dental Journal, vol. 54(9), pp. 661-666 (1988).
Crooks, "CAD/CAM Comes to USC," USC Dentistry, pp. 14-17 (Spring 1990).
Cureton, Correcting Malaligned Mandibular Incisors with Removable Retainers, J. Clin. Orthod, vol. 30, No. 7 (1996) pp. 390-395.
Curry et al., "Integrated Three-Dimensional Craniofacial Mapping at the Craniofacial Research Instrumentation Laboratory/University of the Pacific," Semin. Orthod., 7(4):258-265 (Dec. 2001).
Cutting et a/., "Three-Dimensional Computer-Assisted Design of Craniofacial Surgical Procedures: Optimization and Interaction with Cephalometric and CT-Based Models," Plast. 77(6):877-885 (Jun. 1986).
DCS Dental AG, "The CAD/CAM 'DCS Titan System' for Production of Crowns/Bridges," DSC Production AG, pp. 1-7 (Jan. 1992.
Definition for gingiva. Dictionary.com p. 1-3. Retrieved from the internet Nov. 5, 2004 <http://reference.com/search/search?q=gingiva>.
Defranco et al., "Three-Dimensional Large Displacement Analysis of Orthodontic Appliances," J. Biomechanics, 9:793-801 (1976).
Dental Institute University of Zurich Switzerland, Program for International Symposium JD on Computer Restorations: State of the Art of the CEREC-Method, May 1991, 2 pages total.
Dentrac Corporation, Dentrac document, pp. 4-13 (1992).
DENT-X posted on Sep. 24, 1998 at <http://www.dent-x.com/DentSim.htm>, 6 pages.
Doyle, "Digital Dentistry," Computer Graphics World, pp. 50-52, 54 (Oct. 2000.
DuraClearTM product information, Allesee Orthodontic Appliances—Pro Lab, 1 page (1997).
Duret et al, "CAD-CAM in Dentistry," J. Am. Dent. Assoc. 117:715-720 (Nov. 1988.
Duret et al., "CAD/CAM Imaging in Dentistry," Curr. Opin. Dent., 1:150-154 (1991.
Duret, "The Dental CAD/CAM, General Description of the Project," Hennson International Product Brochure, 18 pages total, Jan. 1986.
Duret,"Vers Une Prosthese Informatisee," (English translation attached), Tonus, vol. 75, pp. 55-57 (Nov. 15, 1985).
Economides, "The Microcomputer in the Orthodontic Office," JCO, pp. 767-772 (Nov. 1979).
Elsasser, Some Observations on the History and Uses of the Kesling Positioner, Am. J. Orthod. (1950) 36:368-374.

English translation of Japanese Laid-Open Publication No. 63-11148 to inventor T. Ozukuri (Laid-Open on Jan. 18, 1998) pp. 1-7.
Faber et al., "Computerized Interactive Orthodontic Treatment Planning," Am. J. Orthod., 73(1):36-46 (Jan. 1978).
Felton et al., "A Computerized Analysis of the Shape and Stability of Mandibular Arch Form," Am. J. Orthod. Dentofacial Orthop., 92(6):478-483 (Dec. 1987.
Friede et al., "Accuracy of Cephalometric Prediction in Orthognathic Surgery," Abstract of Papers, J. Dent. Res., 70:754-760 (1987).
Futterling et a/., "Automated Finite Element Modeling of a Human Mandible with Dental Implants," JS WSCG '98—Conference Program, retrieved from the Internet <http://wscg.zcu.cz/wscg98/papers98/Strasser 98.pdf>, 8 pages.
Gao et al., "3-D element Generation for Multi-Connected Complex Dental and Mandibular Structure," Proc. Intl Workshop on Medical Imaging and Augmented Reality, pp. 267-271 (Jun. 12, 2001).
Gim-Alldent Deutschland, "Das DUX System: Die Technik," 2 pages total (2002).
Gottleib et al., "JCO Interviews Dr. James A. McNamura, Jr., on the Frankel Appliance: Part 2: Clinical 1-1 Management," J. Clin. Orthod., 16(6):390-407 (Jun. 1982).
Grayson, "New Methods for Three Dimensional Analysis of Craniofacial Defoimity, Symposium: Computerized Facial Imaging in Oral and Maxiiofacial Surgery," AAOMS, 3 pages total, (Sep. 13, 1990).
Guess et al., "Computer Treatment Estimates in Orthodontics and Orthognathic Surgery," JCO, pp. 262-28 (Apr. 1989).
Heaven et a/., "Computer-Based Image Analysis of Artificial Root Surface Caries," Abstracts of Papers, J. Dent. Res., 70:528 (Apr. 17-21, 1991).
Highbeam Research, "Simulating Stress Put on Jaw," Tooling & Production [online], Nov. 1996, n pp. 1-2, retrieved from the Internet on Nov. 5, 2004, URL http://static.highbeam.com/t/toolingampproduction/november011996/simulatingstressputonfa . . . >.
Hikage, "Integrated Orthodontic Management System for Virtual Three-Dimensional Computer Graphic Simulation and Optical Video Image Database for Diagnosis and Treatment Planning", Journal of Japan KA Orthodontic Society, Feb. 1987, English translation, pp. 1-38, Japanese version, 46(2), pp. 248-269 (60 pages total.
Hoffmann, et al., "Role of Cephalometry for Planning of Jaw Orthopedics and Jaw Surgery Procedures," 0 (Article Summary in English, article in German), lnfolinatbnen, pp. 375-396 (Mar. 1991.
Hojjatie et al., "Three-Dimensional Finite Element Analysis of Glass-Ceramic Dental Crowns," J. Biomech., 23(11):1157-1166 (1990.
Huckins, "CAD-CAM Generated Mandibular Model Prototype from MRI Data," AAOMS, p. 96 (1999.
Important Tip About Wearing the Red White & Blue Active Clear Retainer System, Allesee Orthodontic Appliances-Pro Lab, 1 page 1998).
JCO Interviews, Craig Andreiko , DDS, MS on the Elan and Orthos Systems, JCO, pp. 459-468 (Aug. 1994).
JCO Interviews, Dr. Homer W. Phillips on Computers in Orthodontic Practice, Part 2, JCO, pp. 819-831.
Jerrold, "The Problem, Electronic Data Transmission and the Law," AJO-DO, pp. 478-479 (Apr. 1988.
Jones et al., "An Assessment of the Fit of a Parabolic Curve to Pre- and Post-Treatment Dental Arches," Br. J. Orthod., 16:85-93 (1989).
Kamada et.al., Case Reports On Tooth Positioners Using LTV Vinyl Silicone Rubber, J. Nihon University School of Dentistry (1984) 26(1): 11-29.
Kamada et.al., Construction of Tooth Positioners with LTV Vinyl Silicone Rubber and Some Case Reports, J. Nihon University School of Denistry (1982) 24(1):1-27.
Kanazawa et al., "Three-Dimensional Measurements of the Occlusal Surfaces of Upper Molars in a Dutch Population," J. Dent Res., 63(11):1298-1301 (Nov. 1984).

(56) References Cited

OTHER PUBLICATIONS

Kesling et al., The Philosophy of the Tooth Positioning Appliance, American Journal of Orthodontics and Oral surgery. 1945; 31:297-304.
Kesling, Coordinating the Predetermined Pattern and Tooth Positioner with Conventional Treatment, KN Am. J. Orthod. Oral Surg. (1946) 32:285-293.
Kleeman et al., The Speed Positioner, J. Clin. Orthod. (1996) 30:673-680.
Kochanek, "Interpolating Splines with Local Tension, Continuity and Bias Control," Computer Graphics, ri 18(3):33-41 (Jul. 1984).
KM Oral Surgery (1945) 31 :297-30.
Kunii et al., "Articulation Simulation for an Intelligent Dental Care System," Displays 15:181-188 (1994).
Kuroda et al., Three-Dimensional Dental Cast Analyzing System Using Laser Scanning, Am. J. Orthod. Dentofac. Orthop. (1996) 110:365-369.
Laurendeau, et al., "A Computer-Vision Technique for the Acquisition and Processing of 3-D Profiles of 7 KR Dental Imprints: An Application in Orthodontics," IEEE Transactions on Medical Imaging, 10(3):453-461 (Sep. 1991).
Leinfelder, et al., "A New Method for Generating Ceramic Restorations: a CAD-CAM2 System," J. Am. 1-1 Dent. Assoc., 118(6):703-707 (Jun. 1989.
Manetti, et al., "Computer-Aided Cefalometry and New Mechanics in Orthodontics," (Article Summary in English, article in German), Fortschr Kieferorthop. 44, 370-376 (Nr. 5), 1983.
McCann, "Inside the ADA," J. Amer. Dent. Assoc., 118:286-294 (Mar. 1989.
McNamara et al., "Invisible Retainers," J. Cfin. Orthod., pp. 570-578 (Aug. 1985).
McNamara et al., Orthodontic and Orthopedic Treatment in the Mixed Dentition, Needham Press, pp. 347-353 (Jan. 1993).
Moermann et al., "Computer Machined Adhesive Porcelain Inlays: Margin Adaptation after Fatigue Stress," IADR Abstract 339, J. Dent. Res., 66(a):763 (1987).
Moles, "Correcting Mild Malalignments—As Easy As One, Two, Three," AOA/Pro Corner, vol. 11, No. 1, 2 pages (2002).
Mormann et al., "Marginale Adaptation von adhasuven Porzellaninlays in vitro," Separatdruck aus: Schweiz. Mschr. Zahnmed. 95: 1118-1129, 1985.
Nahoum, "The Vacuum Formed Dental Contour Appliance," N. Y. State Dent. J., 30(9):385-390 (Nov. 1964).
Nash, "CEREC CAD/CAM Inlays: Aesthetics and Durability in a Single Appointment," Dent. Today, 9(8):20, 22-23 (Oct. 1990).
Nippon Dental Review, "New Orthodontic Device-Dynamic Positioner (D.P.)-I, Approach to the Proposal of D.P. and Transparent Silicone Rubber," 1980, 452: 61-74.
Nippon Dental Review, "New Orthodontic Device-Dynamic Positioner (D.P.)-II, Practice Application and Construction of D.P. and Transparent Silicone Rubber," 1980, 454: 107-130.
Nippon Dental Review, "New Orthodontic Device-Dynamic Positioner (D.P)-III, Case Reports of Reversed Occlusion," 457: 146-164 (Nov. 1980).
Nippon Dental Review, "New Orthodontic Device-Dynamic Positioner (D.P.)—Case Reports of Reversed Occlusion," 1980, 458: 112-129.
Nishiyama et al., "A New Construction of Tooth Repositioner by LTV Vinyl Silicone Rubber," J. Nihon Univ. Sch. Dent., 19(2):93-102 (1977).
Paul et al., "Digital Documentation of Individual Human Jaw and Tooth Forms for Applications in Orthodontics, Oral Surgery and Forensic Medicine" Proc. of the 24th Annual Conf. of the IEEE Industrial Electronics Society (IECON '98), Sep. 4, 1998, pp. 2415-2418.
Pinkham, "Foolish Concept Propels Technology," Dentist, 3 pages total, Jan./Feb. 1989.
Pinkham, "Inventor's CAD/CAM May Transform Dentistry," Dentist, 3 pages total, Sep. 1990.

Ponitz, "Invisible Retainers," Am. J. Orthod., 59(3):266-272 (Mar. 1971).
PROCERA Research Projects, "PROCERA Research Projects 1993—Abstract Collection," pp. 3-728 (1993).
Proffit et al., Contemporary Orthodontics, (Second Ed.), Chapter 15, Mosby Inc., pp. 470-533 (Oct. 1993).
Raintree Essix & ARS Materials, Inc., Raintree Essix, Technical Magazine Table of contents and Essix Appliances, <httpz://www.essix.com/magazine/defaulthtml> Aug. 13, 1997.
Redmond et al., "Clinical Implications of Digital Orthodontics," Am. J. Orthod. Dentofacial Orthop., 117(2):240-242 (2000).
Rekow et a/., "CAD/CAM for Dental Restorations—Some of the Curious Challenges," IEEE Trans. Biomed. Eng., 38(4):344-345 (Apr. 1991).
Rekow et al., "Comparison of Three Data Acquisition Techniques for 3-D Tooth Surface Mapping," LM Annual International Conference of the IEEE Engineering in Medicine and Biology Society, 13(1):344-345 1991.
Rekow, "A Review of the Developments in Dental CAD/CAM Systems," (contains references to LN Japanese efforts and content of the papers of particular interest to the clinician are indicated with a one line summary of their content in the bibliography), Curr. Opin. Dent., 2:25-33 (Jun. 1992).
Rekow, "CAD/CAM in Dentistry: A Historical Perspective and View of the Future," J. Can. Dent. Assoc., 58(4):283, 287-288 (Apr. 1992).
Rekow, "Computer-Aided Design and Manufacturing in Dentistry: A Review of the State of the Art," J. Prosthet. Dent., 58(4):512-516 (Oct. 1987).
Rekow, "Dental CAD-CAM Systems: What is the State of the Art?", J. Amer. Dent. Assoc., 122:43-48 1991).
Rekow, "Feasibility of an Automated System for Production of Dental Restorations, Ph.D. Thesis," Univ. of Minnesota, 244 pages total, Nov. 1988.
Richmond et al., "The Development of a 3D Cast Analysis System," Br. J. Orthod., 13(1):53-54 (Jan. 1986).
Richmond et al., "The Development of the PAR Index (Peer Assessment Rating): Reliability and Validity," Eur. J. Orthod., 14:125-139 (1992).
Richmond, "Recording The Dental Cast In Three Dimensions," Am. J. Orthod. Dentofacial Orthop., 92(3):199-206 (Sep. 1987).
Rudge, "Dental Arch Analysis: Arch Form, A Review of the Literature," Eur. J. Orthod., 3(4):279-284 1981.
Sakuda et al., "Integrated Information-Processing System in Clinical Orthodontics: An Approach with Use of a Computer Network System," Am. J. Orthod. Dentofacial Orthop., 101(3): 210-220 (Mar. 1992).
Schellhas et al., "Three-Dimensional Computed Tomography in Maxillofacial Surgical Planning," Arch. Otolamp!. Head Neck Sur9., 114:438-442 (Apr. 1988).
Schroeder et al., "Algorithms I," The Visualization Toolkit, Chapter 6-9.9, 1996.
Schroeder et al., Eds. The Visual Toolkit, Prentice Hall PTR, New Jersey (1998) Chapters 6, 8 & 9, (pp. 153-210,309-354, and 355-428, respectively.
Segu et al., "Computer-aided Cefalometry and New Mechanics in Orthodontics" (Article Summary in English, article in German), Fortschr. Kieferorthop. 44, 370-376 (Nr. 5), 1983.
Shilliday, (1971). Minimizing finishing problems with the mini-positioner, Am. J. Orthod. 59:596-599.
Siemens, "CEREC—Computer-Reconstruction," High Tech in der Zahnmedizin, 14 pages total (2004).
Sinclair, "The Readers' Corner," J. Clin. Orthod., 26(6):369-372 (Jun. 1992.
Sirona Dental Systems GmbH, CEREC 3D, Manuel utiiisateur, Version 2.0X (in French), 2003,114 pages total.
Stoll et al., "Computer-aided Technologies in Dentistry," (article summary in English, article in German), Dtsch Zahna'rztl Z 45, pp. 314-322 (1990).
Sturman, "Interactive Keyframe Animation of 3-D Articulated Models," Proceedings Graphics Interface '84, May-Jun. 1984, pp. 35-40.

(56) References Cited

OTHER PUBLICATIONS

The Choice Is Clear: Red, White & Blue . . . The Simple, Affordable, No-Braces Treatment, Allesee HI Orthodontic Appliances—Pro Lab product information for doctors. http://ormco.com/aoa/appliances-services/RWB/doctorhtml>, 5 pages (May 19, 2003).

The Choice is Clear: Red, White & Blue . . . The Simple, Affordable, No-Braces Treatment, Allesee HJ Orthodontic Appliances—Pro Lab product information for patients, <http://ounco.com/aoa/appliancesservices/RWB/patients.html>, 2 pages (May 19, 2003).

The Choice Is Clear: Red, White & Blue . . . The Simple, Affordable, No-Braces Treatment, Allesee Orthodontic Appliances—Pro Lab product information, 6 pages (2003).

The Red, White & Blue Way to Improve Your Smile! Allesee Orthodontic Appliances—Pro Lab product information for patients, 2 pages 1992.

Truax L., "Truax Clasp-Less(TM) Appliance System," Funct. Orthod., 9(5):22-4, 26-8 (Sep.-Oct. 1992).

Tru-Tain Orthodontic & Dental Supplies, Product Brochure, Rochester, Minnesota 55902, 16 pages total (1996).

U.S. Department of Commerce, National Technical Information Service, "Automated Crown Replication Using Solid Photography SM," Solid Photography Inc., Melville NY, Oct. 1977, 20 pages total.

U.S. Department of Commerce, National Technical Information Service, "Holodontography: An Introduction to Dental Laser Holography," School of Aerospace Medicine Brooks AFB Tex, Mar. 1973, 37 pages total.

U.S. Appl. No. 60/050,342, filed Jun. 20, 1997, 41 pages total.

Van Der Linden et al., "Three-Dimensional Analysis of Dental Casts by Means of the Optocom," J. Dent. Res., p. 1100 (Jul.-Aug. 1972).

Van Der Linden, "A New Method to Determine Tooth Positions and Dental Arch Dimensions," J. Dent. Res., 51(4):1104 (Jul.-Aug. 1972).

Van Der Zel, "Ceramic-Fused-to-Metal Restorations with a New CAD/CAM System," Quintessence Int., 24(11):769-778 (1993.

Varady et al., "Reverse Engineering Of Geometric Models—An Introduction," Computer-Aided Design, 29(4):255-268,1997.

Verstreken et al., "An Image-Guided Planning System for Endosseous Oral Implants," IEEE Trans. Med. Imaging, 17(5):842-852 (Oct. 1998.

Warunek et al., Physical and Mechanical Properties of Elastomers in Orthodonic Positioners, Am J. Orthod. Dentofac. Orthop. vol. 95, No. 5, (May 1989) pp. 399-400.

Warunek et.al., Clinical Use of Silicone Elastomer Applicances, JCO (1989) XXIII(10):694-700.

Wells, Application of the Positioner Appliance in Orthodontic Treatment, Am. J. Orthodont. (1970) 58:351-366.

Williams, "Dentistry and CAD/CAM: Another French Revolution," J. Dent. Practice Admin., pp. 2-5 (Jan./Mar. 1987.

Williams, "The Switzerland and Minnesota Developments in CAD/CAM," J. Dent. Practice Admin., pp. 50-55 (Apr./Jun. 1987.

Wishan, "New Advances in Personal Computer Applications for Cephalometric Analysis, Growth Prediction, Surgical Treatment Planning and Imaging Processing," Symposium: Computerized Facial Imaging in Oral and Maxilofacial Surgery Presented on Sep. 13, 1999.

WSCG'98—Conference Program, "The Sixth International Conference in Central Europe on Computer Graphics and Visualization '98," Feb. 9-13, 1998, pp. 1-7, retrieved from the Internet on Nov. 5, 2004, URL<http://wscg.zcu.cz/wscg98/wscg98.h>.

Xia et al., "Three-Dimensional Virtual-Reality Surgical Planning and Soft-Tissue Prediction for Orthognathic Surgery," IEEE Trans. Inf. Technol. Biomed., 5(2):97-107 (Jun. 2001.

Yamamoto et al., "Optical Measurement of Dental Cast Profile and Application to Analysis of Three-Dimensional Tooth Movement in Orthodontics," Front. Med. Biol. Eng., 1(2):119-130 (1988).

Yamamoto et al., "Three-Dimensional Measurement of Dental Cast Profiles and Its Applications to Orthodontics," Conf. Proc. IEEE Eng. Med. Biol. Soc., 12(5):2051-2053 (1990).

Yamany et al., "A System for Human Jaw Modeling Using Intra-Oral Images," Proc. of the 20th Annual Conf. of the IEEE Engineering in Medicine and Biology Society, Nov. 1, 1998, vol. 2, pp. 563-566.

Yoshii, "Research on a New Orthodontic Appliance: The Dynamic Positioner (D.P.); I. The D.P. Concept and Implementation of Transparent Silicone Resin (Orthocon)," Nippon Dental Review, 452:61-74 (Jun. 1980.

Yoshii, "Research on a New Orthodontic Appliance: The Dynamic Positioner (D.P.); II. The D.P. Manufacturing Procedure and Clinical Applications," Nippon Dental Review, 454:107-130 (Aug. 1980).

Yoshii, "Research on a New Orthodontic Appliance: The Dynamic Positioner (D.P.); Ill.—The General Concept of the D.P. Method and Its Therapeutic Effect, Part 2. Skeletal Reversed Occlusion Case Reports," Nippon Dental Review, 458:112-129 (Dec. 1980.

Yoshii, "Research on a New Orthodontic Appliance: The Dynamic Positioner (D.P.); Ill. The General Concept of the D.P. Method and Its Therapeutic Effect, Part 1, Dental and Functional Reversed Occlusion Case Reports," Nippon Dental Review, 457:146-164 (Nov. 1980).

You May Be A Candidate For This Invisible No-Braces Treatment, Allesee Orthodontic Appliances—Pro Lab product information for patients, 2 pages (2002).

Anonymous. Straightening Teeth over the Internet; Thousands of Orthodontists Use Web for First Time to Treat Patients. Newswire, Apr. 6, 2000. 2 pages.

"Khanh, T. L. Tran. Innovator is Hoping for a Bite of Braces Market. Wall Street Journal. Oct. 28, 1999, p. B10.".

Rekow et al., "CAD/CAM for Dental Restorations—Some of the Curious Challenges," IEEE Trans. Biomed. Eng., 38(4):314-318 (Apr. 1991).

Wishan, "New Advances in Personal Computer Applications for Cephalometric Analysis, Growth Prediction, Surgical Treatment Planning and Imaging Processing," Symposium: Computerized Facial Imaging in Oral and Maxilofacial Surgery Presented on Sep. 13, 1990.

* cited by examiner

TREATMENT ANALYSIS SYSTEMS AND METHODS

CROSS-REFERENCE

This application is a continuation of U.S. application Ser. No. 12/539,553, filed on Aug. 11, 2009, now U.S. Pat. No. 8,930,219, which is a continuation of U.S. application Ser. No. 09/557,382, filed on Apr. 25, 2000, now abandoned. The contents of each of which are incorporated herein by reference.

BACKGROUND OF THE INVENTION

The invention relates generally to the field of orthodontics and, more particularly, to computer-automated orthodontic treatment of teeth.

Tooth positioners for finishing orthodontic treatment are described by Kesling in the Am. J. Orthod. Oral. Surg., 31:297-304 (1945) and 32:285-293 (1946). The use of silicone positioners for the comprehensive orthodontic realignment of a patient's teeth is described in Warunek et al., J. Clin. Orthod., 23:694-700 (1989). Clear plastic retainers for finishing and maintaining tooth positions are commercially available from Raintree Essix, Inc., New Orleans, La. 70125, and Tru-Tain Plastics, Rochester, Minn. 55902. The manufacture of orthodontic positioners is described in U.S. Pat. Nos. 5,186,623; 5,059,118; 5,055,039; 5,035,613; 4,856,991; 4,798,534; and 4,755,139. Other publications describing the fabrication and use of dental positioners include Kleemann and Janssen, J. Clin. Orthodon., 30:673-680 (1996); Cureton, J. Clin. Orthodon., 30:390-395 (1996); Chiappone J. Clin. Orthodon., 14:121-133 (1980); Shilliday, Am. J. Orthodontics, 59:596-599 (1971); Wells, Am. J. Orthodontics, 58:351-366 (1970); and Cottingham, Am. J. Orthodontics, 55:2331 (1969). Kuroda et al., Am. J. Orthodontics, 110:365-369 (1996) describes a method for laser scanning a plaster dental cast to produce a digital image of the cast. See also U.S. Pat. No. 5,605,459.

U.S. Pat. Nos. 5,533,895; 5,474,448; 5,454,717; 5,447,432; 5,431,562; 5,395,238; 5,368,478; and 5,139,419, assigned to Onnco Corporation, describe methods for manipulating digital images of teeth for designing orthodontic appliances.

U.S. Pat. No. 5,011,405 describes a method for digitally imaging a tooth and determining optimum bracket positioning for orthodontic treatment. Laser scanning of a molded tooth to produce a three-dimensional model is described in U.S. Pat. No. 5,338,198. U.S. Pat. No. 5,452,219 describes a method for laser scanning a tooth model and milling a tooth mold. Digital computer manipulation of tooth contours is described in U.S. Pat. Nos. 5,607,305 and 5,587,912. Computerized digital imaging of the jaw is described in U.S. Pat. Nos. 5,342,202 and 5,340,309. Other patents of interest include U.S. Pat. Nos. 5,549,476; 5,382,164; 5,273,429; 4,936,862; 3,860,803; 3,660,900; 5,645,421; 5,055,039; 4,798,534; 4,856,991; 5,035,613; 5,059,118; 5,186,623; and 4,755,139.

U.S. Pat. No. 5,975,893, assigned to the assignee of the instant invention, describes a system for repositioning teeth using a plurality of individual appliances. The appliances are configured to be placed successively on the patient's teeth and to incrementally reposition the teeth from an initial tooth arrangement, through a plurality of intermediate tooth arrangements, and to a final tooth arrangement. The system of appliances is usually configured at the outset of treatment so that the patient may progress through treatment without the need to have the treating professional perform each successive step in the procedure.

BRIEF SUMMARY OF THE INVENTION

A dental treatment planning system includes an input form to receive one or more dental patient inputs; and an engine adapted to receive the dental patient data from the input form and validating the dental patient data in a predetermined sequence.

Implementations of the system may include one or more of the following. The engine prompts the user for additional data based on previous entries. The treatment includes a diagnostic phase, a goal phase and a treatment path determination phase. The engine checks validity for data entered intra-phase. The validity of the entries is determined by crosschecking against a mutually exclusive condition. The engine checks validity for data entered inter-phase. The engine checks whether the treatment results in an improvement in the patient. The engine checks whether the treatment meets an efficiency guideline or a prudency guideline. The engine can also check the treatment plan against properties of an appliance.

Advantages of the system include one or more of the following. The system improves the accuracy and validity of diagnoses and treatment plan by providing the orthodontist with information and resources to make the measurements that will result in the correct diagnosis.

The system also prevents an orthodontist from entering conflicting diagnoses. Because a patient's teeth and the way they define a bite are interrelated, a series of logical rules are used to crosscheck the diagnoses and to prevent an invalid diagnosis. The system also checks for and requires the entry of a diagnosis for any area for which one is required. This prevents one type of inaccuracy in diagnosis, in that a negative finding is equivalent to an incorrect positive finding.

The system also limits path choices based on the initial and end points for teeth. This prevents an inaccurate path by limiting the path choices to those that head in the correct direction. The system also prevents for the orthodontist from entering two conflicting paths. By cross checking the paths, the system can eliminate invalid paths.

Additionally, certain shortcomings of the appliances with regard to the biology, physics, and mechanics of tooth movement are known. Thus, the system considers the biology, physics, and material of tooth movement in optimizing the treatment plan. The system prevents the orthodontist from entering a goal that is not deemed attainable by the system and the information can be relayed to the doctor when a valid and accurate plan is described that involves these shortcomings. This will allow the doctor to tailor the plan to avoid any pitfalls inherent in the system. Moreover, the system provides feedback, for example direction and education, when the orthodontist is prevented from entering data not allowed by the system. Because there are multiple goals and paths to reach them, a quality result is not guaranteed from an accurate and valid diagnosis. Feedback when a mistake is made in the diagnosis can be used to educate and direct the thinking of the doctor which will perhaps lead to the redevelopment of an entirely new, better, plan, rather than the mere correction of the error which generated the feedback.

In implementations that permit communications over the Internet, the system provides information and assistance 24 hours a day, seven days a week. The system supports a virtual community of dental patients, dentists, specialists such as orthodontists and oral surgeons, financial institutions, benefit providers and the providers of dental equipment or services. For treating professionals, such as dentists and orthodontists, the system provides a one-stop solution for planning patient treatments, managing communication with patients, storing patient records and sharing records with relevant persons outside the doctor's office. The system can act as the repository for the file notes and visual imagery (photographs, x-rays and virtual treatment plans) associated with the course of treatment. The doctors will control access to the centralized patient file. Various tools are provided to support the interpretation of information and the diagnostic process. For example, the system allows the doctors to retrieve, and analyze patient information and to simulate using two and three-dimensional visual imagery of the patient's teeth and other anatomical structures. The system supports visualization of the expected outcome of a particular course of treatment. Working together with the patient these images can enhance the patient's understanding of the benefits of treatment and act as a valuable selling tool for the doctor. The system also provides diagnostic decision-support capabilities such as visualizing the placement of implantations, veneers and crowns before or after a course of treatment to straighten the teeth. The system provides an animated prediction of the suggested treatment that helps the patient and the doctor to visualize the pace of treatment. Using these tools, the doctor can easily and quickly view and/or edit the treatment plan. When doctor and patient choose the final treatment plan the system disseminates aspects of the plan and the relevant patient records to the appropriate members of the virtual community, thus reducing the cost and delay associated with tradition physical shipment of patient information. Aspects of the final treatment plan can be used to generate appliances used in the physical treatment. The information associated with the patient's treatment (visual images, virtual treatment plans, file notes and the like) are digitized and maintained in a central storage facility in a secure manner. Doctors and patients can have access to these files without the need to extract files and models from storage and with reduced risk of records being misplaced.

DETAILED DESCRIPTION OF THE INVENTION

Figure 1:
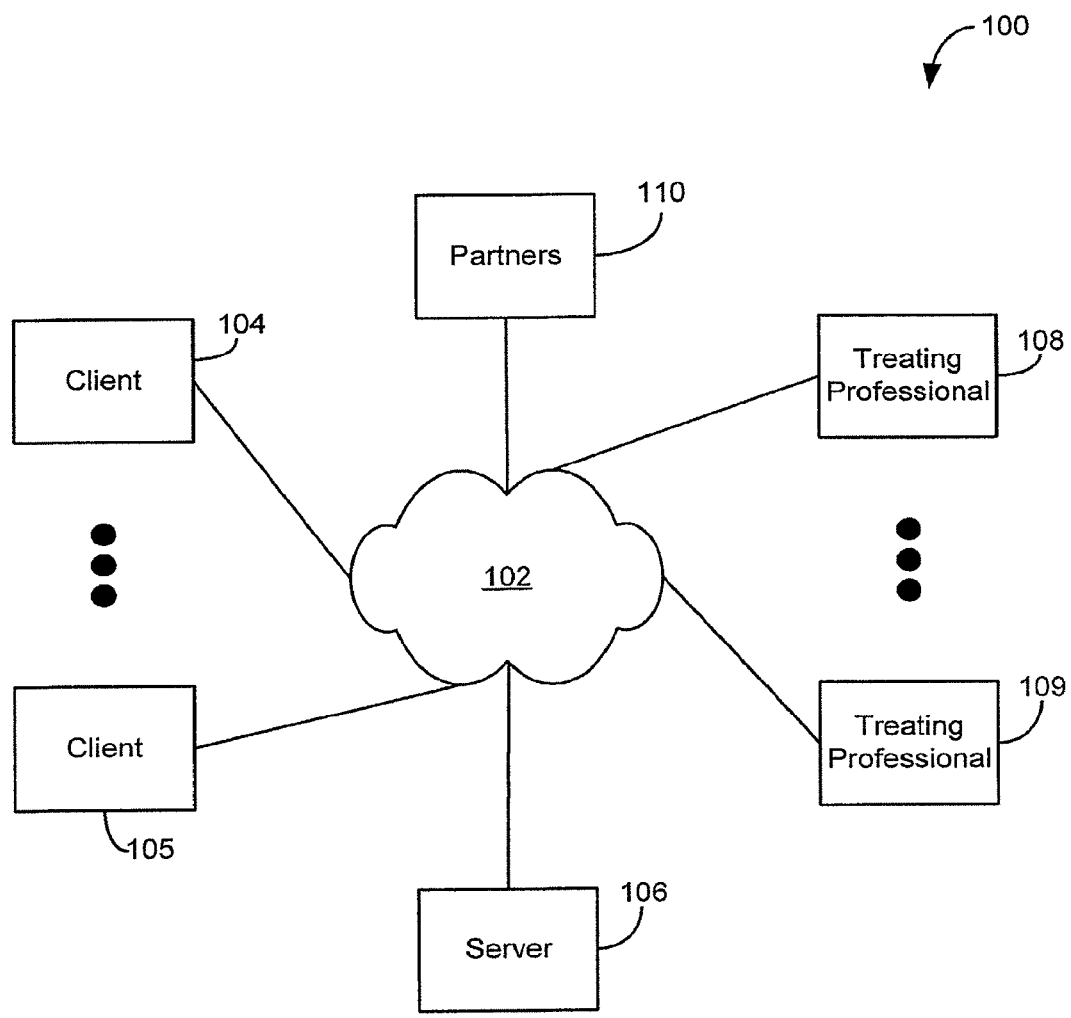
FIG. 1 is a diagram of an exemplary environment supporting electronic commerce.

Referring now to FIG. 1, an environment supporting a dental system 100 is shown. The system 100 communicates over a network 102 that can be a local area network or a wide area network such as the Internet. The Internet has become a significant medium for communication and commerce and has enabled millions of people to share information and conduct business electronically. The unique characteristics of the Internet such as its ability to provide enhanced communication, rich text, and graphic environment provide an ideal support for a wide variety of electronic commerce transactions. The ubiquity and convenience of the Internet makes it ideal for dispensing information on certain topics that traditionally require visits to specialists. For example, certain consumers may be interested in products and services associated with orthodontics and dentofacial orthopedics that specializes in the diagnosis, prevention and treatment of dental and facial irregularities ("malocclusion" or "bad bite"). The orthodontic treatment process typically uses corrective appliances such as braces and/or other fixed or removable appliances to bring the teeth, lips and jaws into proper alignment and to achieve a facial balance. The pervasiveness of the Internet makes it an ideal source for information relating to these products and services.

One or more client computers 104-105 can be connected to the network 102. In one embodiment where the network 102 is the Internet, the client computers execute a suitable browser such as Navigator from Netscape, Inc. and Internet Explorer from Microsoft Corp. By clicking on the highlighted text (or specific graphic image), the user can jump from the current web page to a new web page address associated with the link—with the new page displayed on the screen. In this manner, the user can "surf the web" by clicking on an almost endless succession of links going to page after page all following a common thread as defined by the text or graphic component of the link label.

Through the network 102, the client computers 104-105 can access a dental server 106. The dental server 106 serves a web site, a portal, a vortal, or a content site for providing dental related information to interested parties such as dental patients, dentists, orthodontists, and others. When sensitive information is communicated through the dental server 106, such information is securely encrypted using Secure Sockets Layer (SSL) technology throughout the transaction. The server 106 can be a stand-alone computer or can be a server farm that can distribute processing and communications activity across a computer network so that no single device is overwhelmed. During load balancing, if one server is swamped with requests, excess requests are forwarded to another server with more capacity.

The network 102 connects the dental server 106 to one or more treating professional workstations 108-109. The workstations 108-109 allow treating professionals access to a plethora of services provided by the dental server 106 such as patient treatment and office management, among others. The dental server 106 stores information associated with patient history on-line in a secure manner. The server 106 also allows the treating professional to have a comprehensive view of the patient's treatment history at any time using a suitable browser, eliminating the need to pull treatment files or charts or to look for misfiled or lost charts. The dental server 106 also provides treating professionals with tools to analyze patient data, for example, tools to reconstruct a 3D model of the teeth. For example, using the browser, the treating professional can request the server 106 to animate the progress of the treatment plan. When the treating professional arrives at a prescription or other final designation, the treatment prescription is used to automatically generate appliances, as described in more details below. Further, in addition to aiding professionals in treating patients, the treating professional can perform office management, purchasing and other logistical operations using the browser and the dental server 106.

In addition to communicating with patients and treating professionals, the dental server 106 can communicate with one or more partners 110 using the network 102. The partners 110 can be product suppliers, service providers, or any suitable commercial entities. Other possible partners include value-added service providers such as third party software providers who provide plug-in viewing and diagnostic enhancements that can be used by the professionals.

In combination, the dental server 106 forms a hub that links dental clients using client computers 104-105, treating professionals using workstations 108-109, and partners 110 into a living electronic commerce (e-commerce) community.

Figure 2:
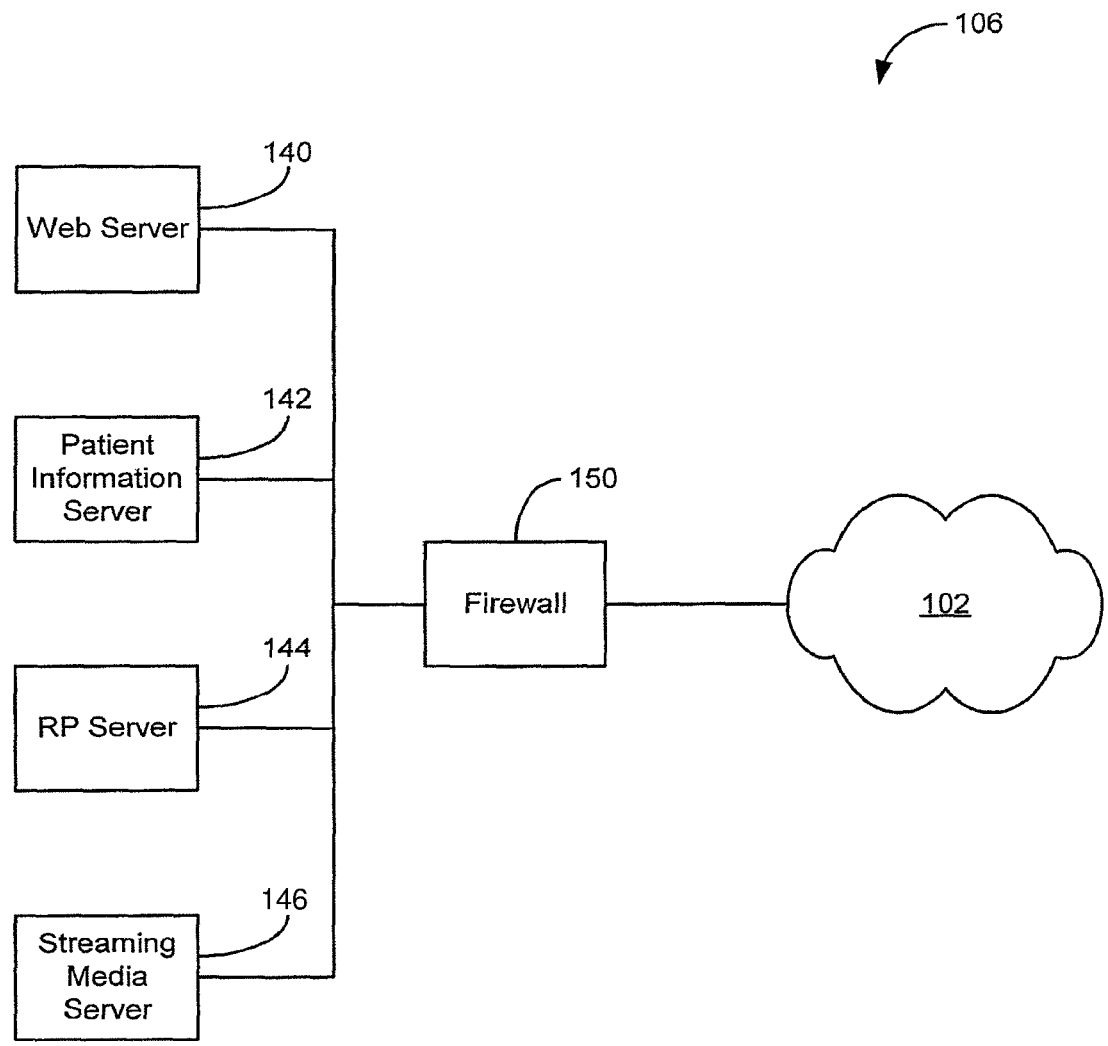
FIG. 2 is a diagram of a server to support electronic commerce.

FIG. 2 shows an embodiment of the server 106. The server 106 includes a web server 140, a patient information server 142, a resource planning (RP) server 144 and a streaming server 146. In one embodiment, the RP server 144 runs Microsoft SQL server and provides information relating to a doctor or a patient such as address and history. See, for example, Table 1. When a patient's case or static snapshots of the case is needed, the data is pulled from the patient information server 142. When media data such as video needs to be streamed to a requesting client, the streaming server 146 can send the stream. In one implementation, the streaming data is stored in QuickTime format on a Linux-based server running the QuickTime server software.

TABLE 1

| Case Type<br>Question Prompts/Printed Statements | Answer Choices |
| --- | --- |
| Please select which Align<br>Recommended<br>Treatment case your patient best<br>represents.<br>Click all that apply. | Mild Spacing<br>Moderate Spacing<br>Mild Crowding |
|  | Moderate Crowding<br>Narrow Arch<br>Post-orthodontic<br>Relapse |

The servers can be clustered. In one embodiment using Microsoft's Cluster Server, cluster-enabled applications such as Microsoft's SQL Server and Exchange. With Cluster Server, two servers can run applications at the same time. When one server fails, the remaining server handles its application as well as the failed server's applications. Next, the remaining server adopts the IP address of the failed server and mounts one or more data drives that the two systems share. The remaining server is rebooted and applications such as SQL Server can be started and initialized on this server. Persistent clients can re-attach to the server and continue to operate.

Figure 3:
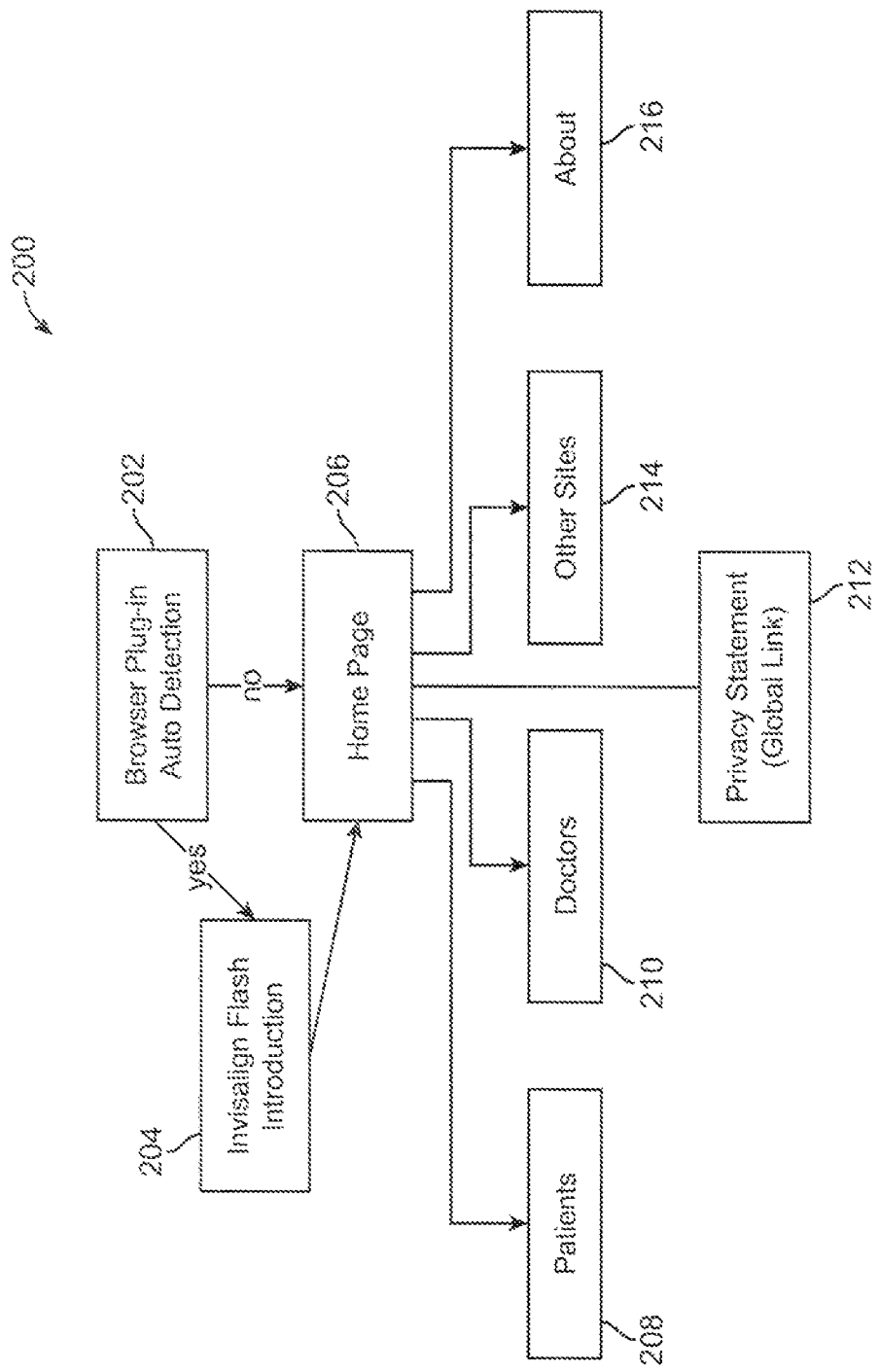
FIG. 3 is a diagram of a web site on the server of FIG. 2.

Referring now to FIG. 3, a diagram 200 shows various major functions supported by the dental server 106. First, the process 200 performs an automatic detection for the existence of a browser welcome plug-in (step 202). If the welcome plug-in exists, an introductory animation (flash) is shown (step 204). From step 202 or 204, the process 200 shows a home page (step 206) with one or more links. A link is created by having a word in a text field (or a graphic image on a web page) linked to the location of another web page, via a string of information setting forth the new web page address presented in hypertext transfer protocol (HTTP), among others.

The user can navigate the home page to join a particular site from a constellation of related sites. For instance, the user can navigate to a patient's site (step 208), a doctor's site (step 210), a privacy statement site (step 212), one or more additional sites (step 214), and an about site (step 216), among others. The additional sites can be an on-line shopping store that is co-branded with the web site hosted by the server 106, or the on-line shopping store can be directly affiliated with a third party such as planet-rx.com, among others. The additional sites can also be third party value-added providers of products and/or services.

Figure 4:
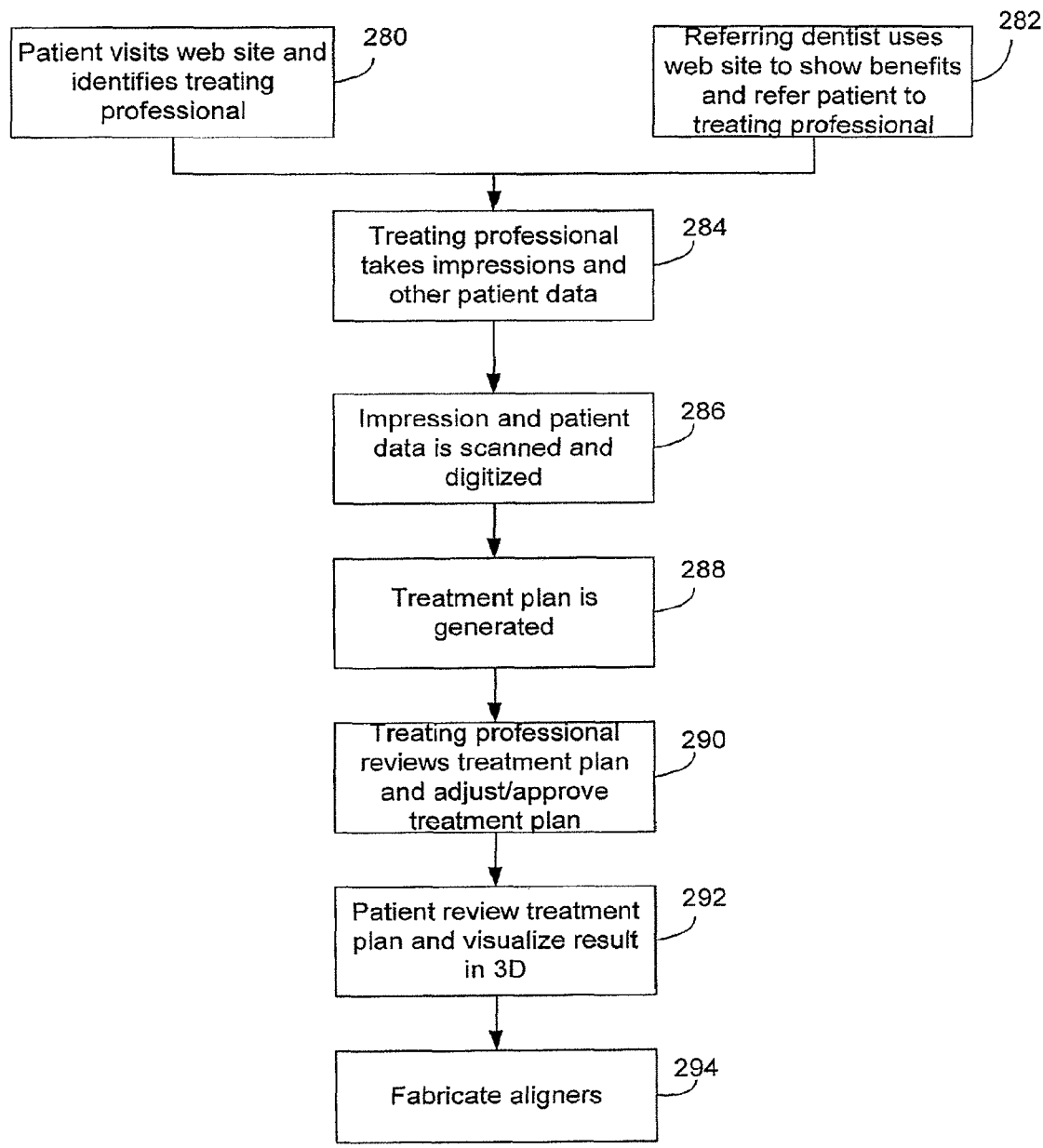
FIG. 4 is a flowchart of a process for a patient receiving dental treatment.

FIG. 4 illustrates an exemplary usage of the system of FIG. 1 from a treating professional's perspective. A prospective patient uses a client computer 104 and visits the web site on the dental server 106 (step 280). The client identifies a treating professional and schedules an appointment with the treating professional. Alternatively, a referring dentist can refer the client to the treating orthodontist (step 282). The referring dentist can visit the web site on the dental server 106 and uses one or more dental esthetic tools to show patients the potential benefits of anterior and posterior esthetic restorations and, if the patient is interested, refers the patient to the treating professional.

During an initial examination, the treating professional or an assistant takes a set of digital facial and intraoral images which is uploaded to a secure, collaborative workspace on the dental server 106 (step 284). The workspace is shared with the referring dentist.

Next, the treating professional generates a dentofacial treatment visualization showing the patient's face and smile before and after treatment (step 286). The treating professional can also combine the patient's face and an aligner into the intraoral image to show how the inconspicuous the appliance will be (step 288).

Once the patient requests treatment, the treating professional takes impressions and a bite registration and sends the information to the company (step 290). The treating professional also takes a lateral ceph and a panorex and uploads them and a treating prescription to the workspace (step 292). The professional's assistant creates a separate workspace for the patient, uploads selected "before and after" images into it, and invites the patient to review the images (step 294).

At the company, another professional reviews the records and decides to accept or decline the case. The models are then scanned, and the intraoral images are retrieved and used to texture-map enamel and gingiva. The data is then sent to the workspace and the treating professional is notified.

In one embodiment, the tooth models may be posted on a hypertext transfer protocol (http) web site for limited access by the corresponding patients and treating clinicians. Since realistic models have a large volume of data, the storage and transmission of the models can be expensive and time consuming. To reduce transmission problems arising from the large size of the 3D model, in one embodiment, data associated with the model is compressed. The compression is done by modeling the teeth meshes as a curve network before transmission to the treating professional. Once the curve network is received, the 3D model is reconstructed from the curve network for the treating professional to analyze. More information on the compression is disclosed in a co-pending application having Ser. No. 09/506,419, entitled, "EFFICIENT DATA REPRESENTATION OF TEETH MODEL", and filed by ELENA PAVLOVSKAIA and HUAFENG WEN on Feb. 17, 2000, the contents of which are hereby incorporated.

The treating professional can, at his or her convenience, check the setup, and review the information sent in step 300

(step 302). The treating professionals can use a variety of tools to interpret patient information. For example, the treating professional can retrieve and analyze patient information through a reconstructed 3D model of the patient's teeth and other anatomical structures. The professional can view animations showing the progress of the treatment plan to help the treating physician visualize the pace of treatment. Using these tools, the treating professional can easily and quickly view and/or edit the treatment plan.

If necessary, the treating professional can adjust one or more teeth positions at various intermediate stages of treatment (step 302). A variety of diagnostic decision-support capabilities such as automated teeth collision detection can be used to aid the treating professional in adjusting the teeth positions.

When the treating professional arrives at a prescription or other final designation, the treatment information is automatically collected by the system over the Internet, thus eliminating the cost and delay associated with the traditional physical shipping of patient information (step 304). These modifications are then retrofitted onto the dataset used to generate the aligners (step 306).

In order for the orthodontist to treat a case, the orthodontist needs to generate a treatment plan, typically after performing an initial diagnosis. A correct initial diagnosis is needed for certain orthodontic appliances such as the Invisalign appliances from Align Technology, Inc. of Sunnyvale, Calif. To optimally use the Invisalign treatment, the orthodontist needs to accurately define the course of treatment at time zero. The interrelationship of all of the teeth to form a particular bite allows the initial diagnoses to be checked against each other for validity. However, the entire set of diagnoses can be inaccurate together, and would not be caught by such a crosscheck.

Figure 5:
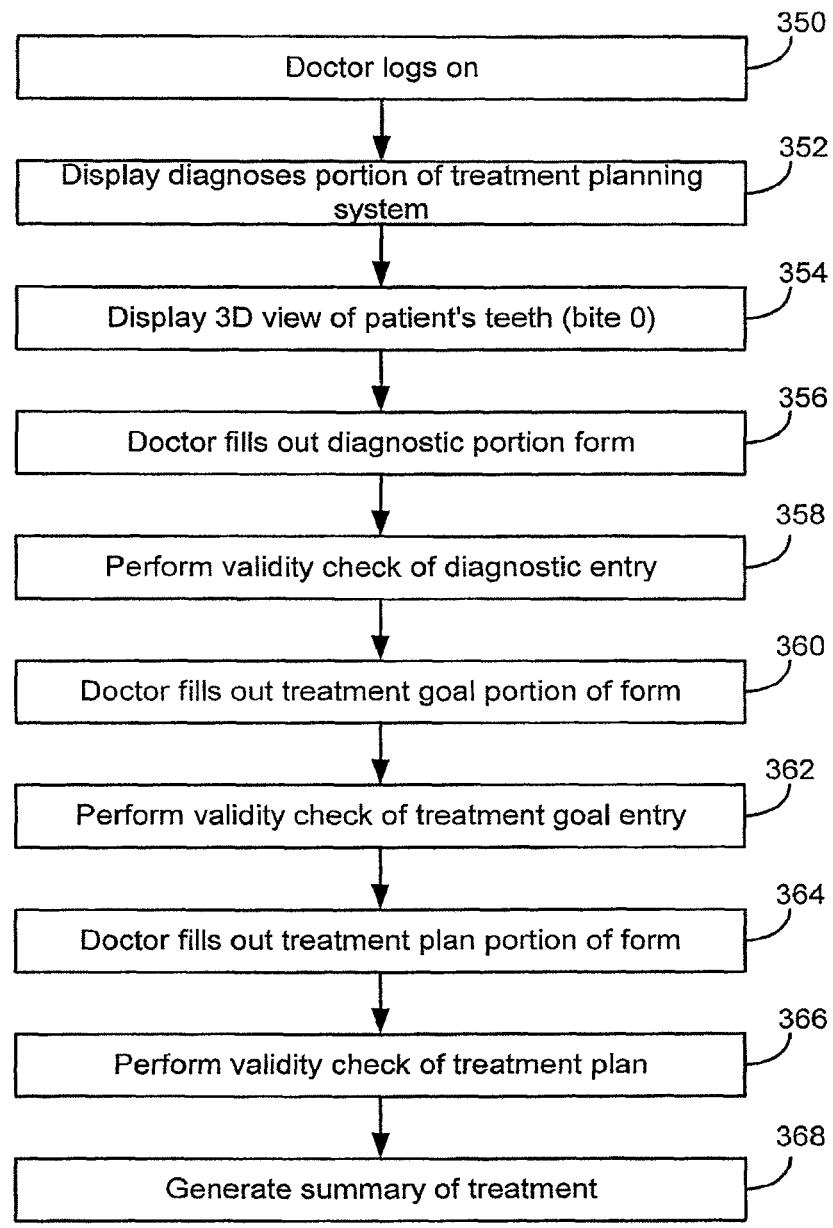
FIG. 5 is a flowchart of a process for a treating a dental patient.
Figure 6:
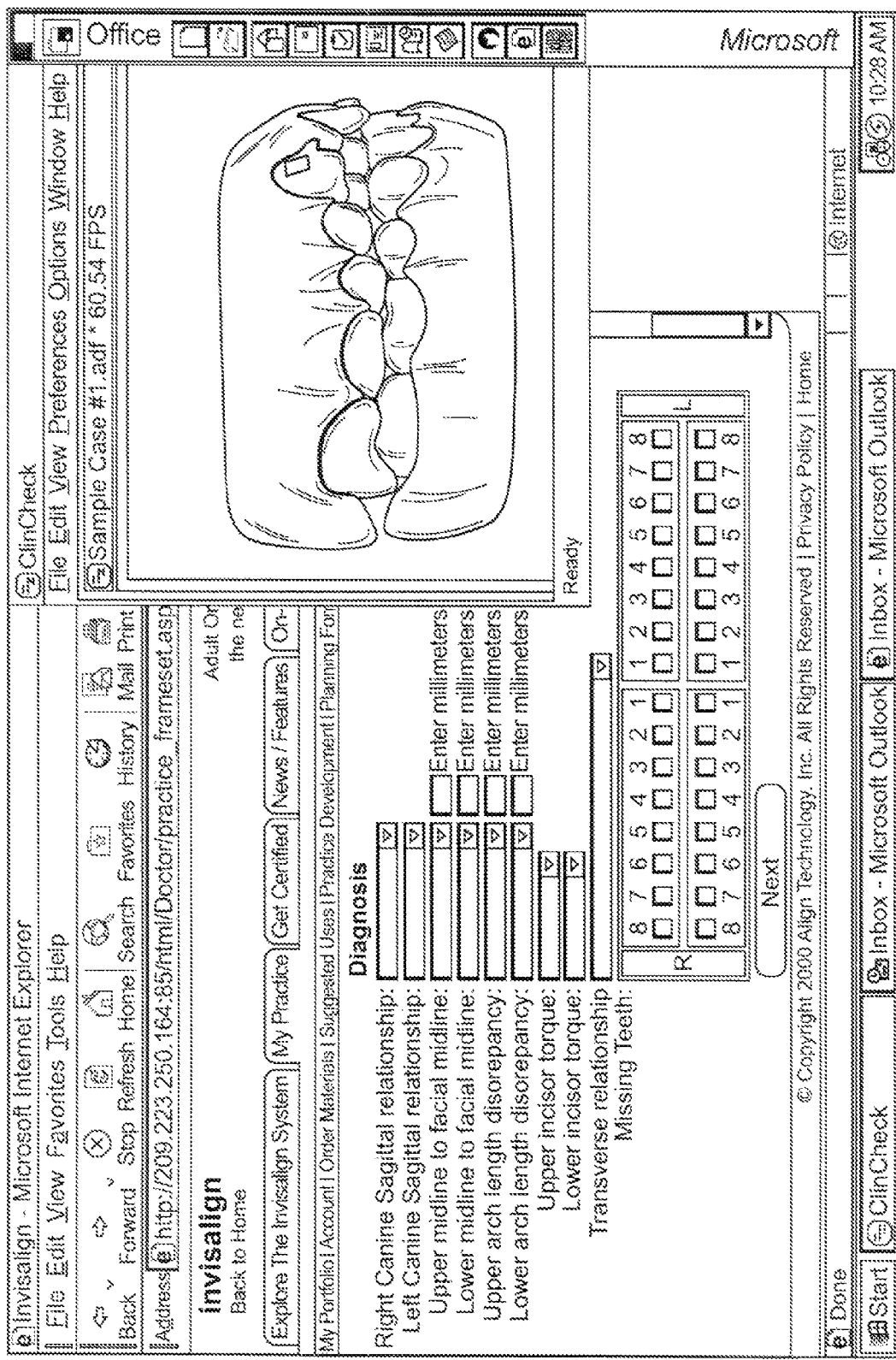
FIG. 6 is an exemplary output showing a treatment plan form and a 3D view of teeth with a browser.

FIG. 5 shows a process for treating teeth. First, a treating professional such as an orthodontist or a doctor logs on to a treatment planning system (step 350). Next, a diagnosis portion of the treatment planning system is displayed (step 352). Also, the system displays a 3D view of the patient's teeth (step 354). In this case, a static bite 0 image is displayed. The bite 0 image refers to the position the teeth are in at time zero, or the pretreatment state. The rendering of the 3D view of the teeth focuses the doctor on problems that need to be addressed. The teeth displayed on the screen are the actual teeth and bite that will be used to generate the treatment. Because of this, the doctor is able to accurately plan the treatment by using this view of the teeth, as opposed to previously taken photos of the teeth. An exemplary user interface at step 354 is shown as FIG. 6. This window of the teeth shows a 3D rendering of the patient's teeth, which can be moved in all three planes of space to gain a better view. The window can also be opened to show further visual diagnostic data such as patient X-rays, photos, or any other data useful for the diagnostic process.

Referring back to FIG. 5, the system prompts the doctor to fill-out the diagnostic portion of the form (step 356). See, for example, Tables 2 and 3. The diagnostic portion of the form requires that the doctor input data relating to the teeth which are present, their condition, their position in the dental arches, their relationship to each other, their size, and their alignment. Once the diagnostic portion of the form has been entered, the system performs a validity check of the diagnostic entry (step 358). The entered data can be crosschecked against Align Technology's case selection criteria to ensure that the submitted case is acceptable for treatment.

TABLE 2

| | Doctor & Patient Information Question Prompts/Printed Statements | Answer Choices |
|---|---|---|
| A | Doctor's Name | |
| B | Street Address | |
| C | City, State, Zip | |
| D | Phone | |
| E | email | |
| E1 | FAX | |
| E2 | Contact Person | |
| F | Patient's Name | |
| G | Age | |
| H | Gender | |
| H1 | Chief Concern (Function) Calculate patients age. | Print patient's age. |

TABLE 3

| | Diagnosis Question Prompts/ Printed Statements | Answer Choices | |
|---|---|---|---|
| I | Right Canine Sagittal relationship | 2 | Full Class II |
| | | 5 | End on Class II |
| | | 7 | 2 mm Class II |
| | | 8 | 1 mm Class II |
| | | 9 | Solid Class I |
| | | 10 | 1 mm Class III |
| | | 11 | 2 mm Class III |
| | | 13 | End on Class III |
| | | 16 | Full Class III |
| J | Left Canine Sagittal relationship | 2 | Full Class II |
| | | 5 | End on Class II |
| | | 7 | 2 mm Class II |
| | | 8 | 1 mm Class II |
| | | 9 | Solid Class I |
| | | 10 | 1 mm Class III |
| | | 11 | 2 mm Class III |
| | | 13 | End on Class III |
| | | 16 | Full Class III |
| K | Upper midline to facial midline | Centered | |
| | | Displaced right | Enter millimeters |
| | | Displaced left | Enter millimeters |
| L | Lower midline to facial midline | Centered | |
| | | Displaced right | Enter millimeters |
| | | Displaced left | Enter millimeters |
| M | Upper arch length discrepancy | None | |
| | | Spacing | Enter millimeters |
| | | Crowding | Enter millimeters |
| N | Lower arch length discrepancy | None | |
| | | Spacing | Enter millimeters |
| | | Crowding | Enter millimeters |
| O | Upper incisor torque | Normal Proclined Retroclined | |
| P | Lower incisor torque | Normal Proclined Retroclined | |
| P1 | Transverse relationship | Upper and lower in good relationship Maxilla is narrower Mandible is narrower | |

TABLE 3-continued

| | Diagnosis Question Prompts/ Printed Statements | Answer Choices |
|---|---|---|
| Q | Missing teeth | Indicate on grid |
| R | Crowns/bridges/facial restorations | Indicate on grid |
| R1 | Tooth size discrepancy | Indicate teeth on grid |
| R2 | Ankylosed/impacted teeth | Indicate teeth on grid |
| R3 | CR/CO shift? | No |
| | | Yes |
| | (Function) If R3 = "Yes" then | Print "Please note that Align currently only recommends treatment from the CO position." |

The system then displays a treatment goal portion of the form and requests the doctor to fill this portion of the form (step 360). See, for example, Table 4. The system then performs a validity check of the treatment goal entry (step 362). Because of the fact that the teeth are all related to each other by virtue of their position, it is possible to cross check the entered treatment goal data against itself, as well as against the previously entered diagnostic data. Additionally, it allows a cross check against Align Technology's case selection criteria for what is possible with the system. Thirdly, the answers from each question prompt specific subsequent questions. For example, when a treatment goal input is given, the system checks that the input is compatible with previous diagnostic input, that the treatment goal is realistic with what Align Technology deems acceptable, and that the treatment goal is compatible with other previously entered treatment goals. The data that has been input will generate further questions, and eliminate possible questions that do not have to do with that particular patient.

TABLE 4

| | Treatment goals Question Prompts/Printed Statements | Answer Choices | |
|---|---|---|---|
| R2 | Treat arches | Both | |
| | | Upper only | |
| | | Lower only | |
| R3 | For limited treatment treat at least | Indicate teeth on grid | |
| S | Right Canine Sagittal Relationship | 0 | Maintain |
| | | 2 | Full Class II |
| | | 5 | End on Class II |
| | | 7 | 2 mm Class II |
| | | 8 | 1 mm Class II |
| | | 9 | Solid Class I |
| | | 10 | 1 mm Class III |
| | | 11 | 2 mm Class III |
| | | 13 | End on Class III |
| | | 16 | Full Class III |
| | (Function) If S = 0 or if S-I = 0 then go to V | | |
| | (Function) If ABS (S-I) > 3 then | Print "The Invisalign System is not currently recommended for such a large sagittal change. Please attempt a smaller change." | Go to S |
| | (Function) If R2 = "Lower only" and S-I > 0 then | Print "Sagittal cannot be changed without treating upper." | Go to S |
| | (Function) If R2 = "Lower only" and S-I < or = 0 then | Go to U | |
| | (Function) If R2 = "Upper only" and S-I < 0 then | Print "Sagittal cannot be changed wit out treating lower." | Go to S |
| | (Function) If R2 = "Upper only" and S-I > or = 0 then | Skip U | |
| T | If I-S < 0 then | Achieve sagittal change by Check all that apply | Distalize upper molars |
| | | | Lower posterior interproximal reduction |
| | | | Upper posterior interproximal reduction |
| U | If I-S > 0 then | Achieve sagittal change by | Distalize lower molars |
| | | | Lower posterior interproximal reduction |
| | | | Upper posterior interproximal reduction |

TABLE 4-continued

| | Treatment goals Question Prompts/Printed Statements | | Answer Choices | |
|---|---|---|---|---|
| V | Left Canine Sagittal Relationship | 0 | Maintain | |
| | | 2 | Full Class II | |
| | | 5 | End on Class II | |
| | | 7 | 2 mm Class II | |
| | | 8 | 1 mm Class II | |
| | | 9 | Solid Class I | |
| | | 10 | 1 mm Class III | |
| | | 11 | 2 mm Class III | |
| | | 13 | End on Class III | |
| | | 16 | Full Class III | |
| | (Function) If V = 0 or if V-J = 0 then go to Y | | | |
| | (Function) If ABS(V-J) > 3 then | print "The Invisalign System is not currently recommended for such a large sagittal change. Please attempt a smaller change." | Go to V | |
| | (Function) If R2 = "Lower only" and V-J > 0 then | Print "Sagittal cannot be changed without treating upper." | Go to V | |
| | (Function) If R2 = "Lower only" and V-J < or = 0 then | Go to W | | |
| | | Print "Sagittal cannot be changed without treating lower." | Go to V | |
| | If R2 = "Upper only" and V-J > or = 0 then | Skip X | | |
| W | If J-V < 0 then | Achieve sagittal change by | Distalize upper molars | |
| | | | Lower posterior interproximal reduction | |
| | | | Upper posterior interproximal reduction | |
| X | If J-V > 0 then | Achieve sagittal change by | Distalize lower molars | |
| | | | Lower posterior interproximal reduction | |
| | | | Upper posterior interproximal reduction | |
| Y | If M = "Spacing" then | Eliminate upper spacing by Check all that apply | Maximum anchorage (Retract anteriors) Reciprocal closure Minimum anchorage (Protract molars) | |
| AB | If M = "Crowding" then | Reduce upper crowding by Check all that apply | Torque anteriors Expand posteriors | |
| | | | Interproximal reduction | Indicate on grid |
| AC | If N = "Crowding" then | Reduce lower crowding by Check all that apply | Torque anteriors Expand posteriors | |
| | | | Interproximal reduction | Indicate on grid |
| | | | Extract lower incisor | Indicate on grid |
| AD | If N = "Spacing" then | Close spaces with Check all that apply | Maximum anchorage (Retract anteriors) Reciprocal closure Minimum anchorage (Protract molars) | |
| | (Function) If P1 = "Upper and Lower in good relationship" and either AA or AB = "expand posteriors" but not both, then | print "You must expand both arches, or neither, to preserve transverse" | | |

TABLE 4-continued

| | Treatment goals Question Prompts/Printed Statements | Answer Choices | | |
|---|---|---|---|---|
| AE | If RI has information then | Relieve tooth size discrepancy by | Leave space | indicate on grid |
| | | check all that apply | Interproximal reduction | indicate on grid |
| AF | | Curve of Spee | Level (may require attachments) Maintain | |
| | (Function) If AF = Maintain and S-I not = and V-J not 0 then | Print "A less than flat Curve of Spee may prevent achieving sagittal correction." | | |
| AG | If P1 = "Maxilla Narrower" then | Correct transverse relationship by | Expand maxilla | |
| AH | If P1 = "Mandible Narrower" then | Correct transverse relationship by | Constrict maxilla | |
| | | Check all that apply | Expand mandible | |
| AI | Special instructions | Free form text box | | |
| AJ | Will the patient object if attachments are placed? | | Please don't use attachments | |
| | (Align will place them only as needed. Results may be compromised if not used.) | | Attachments are fine. | |
| AK | Has this patient's case been shipped to Align before? | | Yes | |
| | | | No | |
| AJ | Aligner shipment timing | PreCheck (sets 1-3 arrive in 6 weeks, prior to ClinCheck approval) | | |
| | | Standard (sets 1-12 arrive in 8 weeks) | | |

The system then displays a treatment plan portion of the form and requests the doctor to fill this portion of the form (step 364). The form now knows the start point of all the teeth (from the diagnostic portion) and the end point (from the treatment goal portion). Specific questions are generated to guide the doctor through a plan for how to get the teeth from their start to end position. The system then performs a validity check of the treatment plan entry (step 366). This validity check ensures that the doctor does not enter two incompatible answers that would involve the teeth running into each other, or not heading in the direction of the goal, etc.

Additionally, the system generates a summary of the treatment plan (step 368). The summary consists of all of the input of the treatment planning form. It is designed for review by the doctor to allow the doctor to review all of the entered data and ensure that it is in accordance with what he intended.

Figure 7:
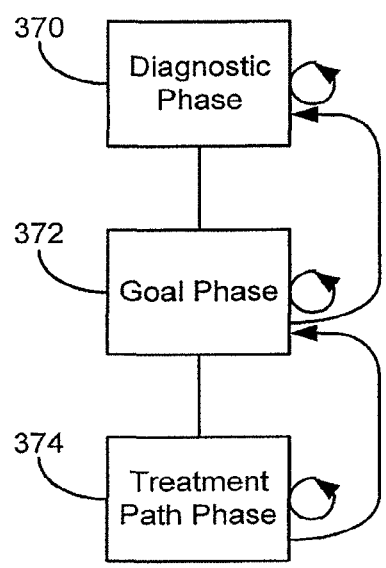
FIG. 7 is a flowchart of a process to diagnose and generate a patient treatment plan.

FIG. 7 shows various phases associated with a treatment plan. First, the system captures data relating to a diagnostic phase (step 370). The system performs validity check on the received data before proceeding to the next phase.

After validating diagnostic phase data, the system then captures data relating to a diagnostic phase (step 372). The system performs validity check on the received data for the current phase (intra-phase) as well as checking for proper relationships between phases (inter-phase) before proceeding to the next phase.

After validating goal phase data and checking for proper relationship between the diagnostic phase and the goal phase, the system then captures data relating to a treatment path phase (step 374). Again, the system performs validity check on the received data for the current phase (intra-phase) as well as checking for proper relationships between phases (inter-phase) before generating the treatment plan.

Figure 8:
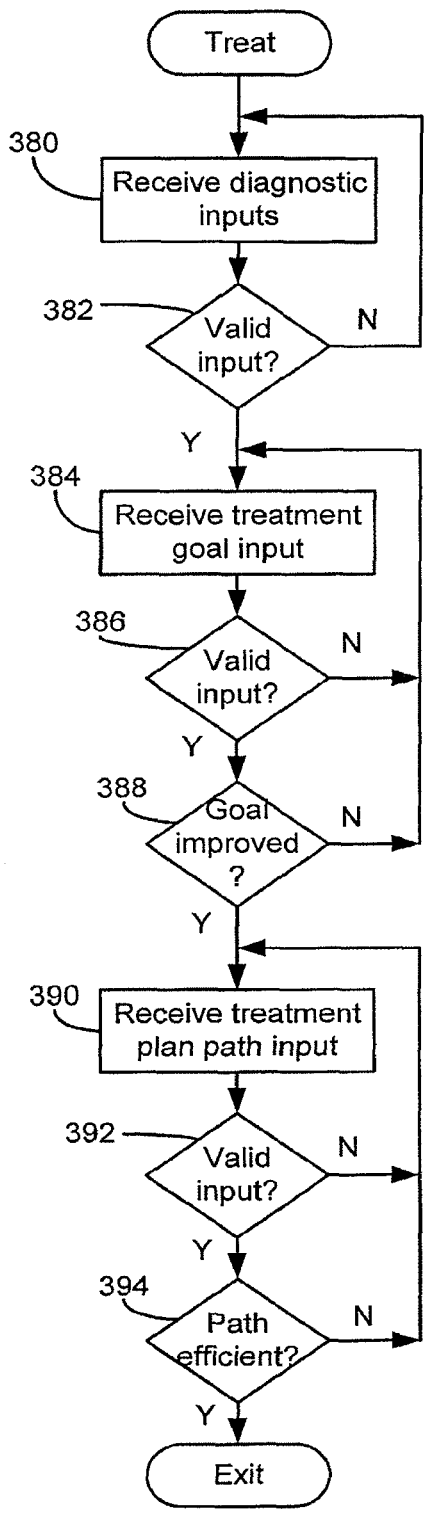
FIG. 8 is one exemplary implementation of FIG. 7.

FIG. 8 shows an embodiment of the flowchart of FIG. 7. First, the process of FIG. 8 receives diagnostic data (step 380). Next, the process checks whether the data is valid (step 382). If not, the process loops back to step 380 to validate data for the diagnostic phase.

From step 382, if the data is valid, the process receives treatment goal input data (step 384). Next, the process checks for valid data (step 386). If the data is invalid, the process loops back to step 384 to collect and validate the goal input data.

From step 386, if the data is valid, the process also checks that the treatment goal improves the patient's condition (step 388). If the treatment goal fails to improve the patient, the process loops back to step 384 to prompt the user to update the treatment goal and to validate the treatment goal once more.

From step 388, the process of FIG. 8 receives treatment plan path input data from the user (step 390). Next, the process validates the treatment plan path data (step 392). From step 392, the process also checks to ensure that the proposed path results in a treatment that is efficient and that follows a desired order (step 394). If the path is undesirable, the process of FIG. 8 loops back to step 390 to receive updated treatment plan path data. Alternatively, if the path is acceptable, the process exits.

As an example, a doctor may enter, among other things, the following information: Diagnosis; Right Canine Sagittal relationship: End on Class II (This describes the relationship of the bite of the top teeth to the bottom teeth); Left Canine Sagittal relationship: Class I (This describes the relationship of the bite of the top teeth to the bottom teeth); Maxillary midline in relation to face: Centered (This describes the relationship of the middle of the upper front teeth in relationship to the middle of the face); Mandibular midline in relation to face: Centered (This describes the relationship of the middle of the lower front teeth in relationship to the middle of the face); Maxillary arch length: Crowding, 9 mm (This qualifies and quantifies the discrepancy between the total size of the teeth and the total space available for them in the mouth); Mandibular arch length: Crowding, 3 mm (This qualifies and quantifies the discrepancy between the total size of the teeth and the total space available for them in the mouth).

In this example, the system processes the entries as they are entered, and the doctor is informed to check midlines (right and left sagittal asymmetric, but midlines don't reflect asymmetry). This is because the teeth are being described as one thing, but from three different views. If the system determines that one of the views doesn't match the other two, the doctor is informed. In this way the form checks for intraphase validity. In one condition, the form can inform the doctor that, "Treatment is not recommended for crowding in any arch greater than 6 mm," because 6 mm has been decided to be the cutoff point for acceptability.

Once achieving a sound diagnosis, the doctor would then be permitted to enter the treatment goals. In this example, the doctor enters the following as the goals: (1) Right canine sagittal relationship: Class I; (2) Left canine sagittal relationship: Maintain; and (3) Treat arches: Lower only (In other words, do not do anything with the top teeth).

In this example, the system notifies the doctor that, "The system does not recommended the sagittal changes of the magnitude requested on the right side," because the distance the teeth need to go from the diagnostic position to the goal position of Class I is too great to be permitted by the appliance. The system would also instruct the doctor that the upper arch needs to be treated to achieve a sagittal change.

Now, assuming legitimate responses have been registered, the start point (diagnosis) and end point (goal) have been established, and the path between the two can be delineated by a list of questions generated in the previous responses. An exemplary treatment plan is (1) Achieve right sagittal change by: Distalize upper molars (A treatment which positions the teeth on the right side to match with the unmoved lower teeth) (2) Relieve maxillary crowding by: Procline incisors; and (3) Relieve mandibular crowding by: Procline incisors.

In one embodiment, the system asks a series of other questions regarding timing of the product delivery, etc. A summary will then be displayed regarding all of the inputs such that the doctor can confirm the entries.

Figure 9:
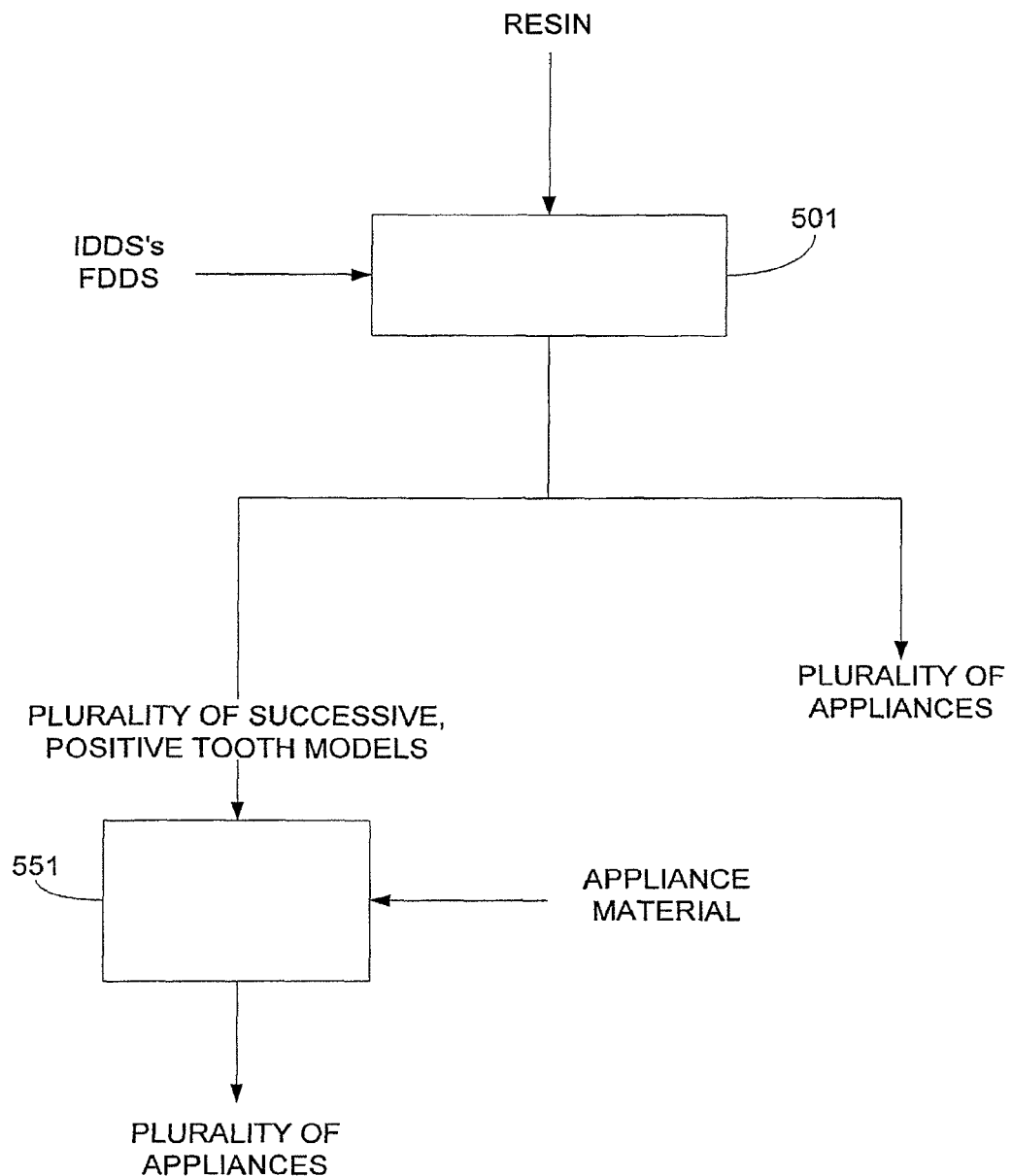
FIG. 9 is a diagram of a system for manufacturing appliances.

FIG. 9 shows a process 400 associated with a viewer that allows the treating professional to visualize the patient's teeth over the network 102 such as the Internet. In one embodiment, during start-up, a browser checks for a viewer plug-in module embodying the process 400 in a "plug-ins" subdirectory (Windows) or Plug-ins folder (Mac OS) in the same folder or directory as the browser (step 402). If the viewer plug-in module is available, the browser looks for a MIME type and extension info from the version resource. Through a TYPE attribute, the browser knows the MIME type and can load a registered plug-in first and, if there are no matches for the MIME type, the browser looks for a helper application.

Once the viewer plug-in is identified, the browser loads the viewer plug-in code into memory (step 404); initializes the viewer plug-in (step 406); and creates a new instance of the viewer plug-in (step 408). When the professional leaves the site or closes the window, the viewer plug-in instance is deleted. When the last instance of the viewer plug-in is deleted, the plug-in code is unloaded from memory.

Next, data files are downloaded to the viewer plug-in (step 410). In one implementation, the viewer plug-in downloads a data file from the dental server 102 using a suitable protocol such as a file transfer protocol (FTP). The viewer plug-in uses the downloaded file to present the treatment plan graphically to the clinician. The viewer plug-in also can be used by the treatment plan designer at the host site to view images of a patient's teeth. FIG. 8 shows an exemplary user interface for the viewer plug-in of FIG. 3. The professional can change views, select a particular tooth and change its position as desired (step 412). 3-D images of various orthodontic views can then be rendered after each instruction from the treating professional is received (step 414).

Figure 10:
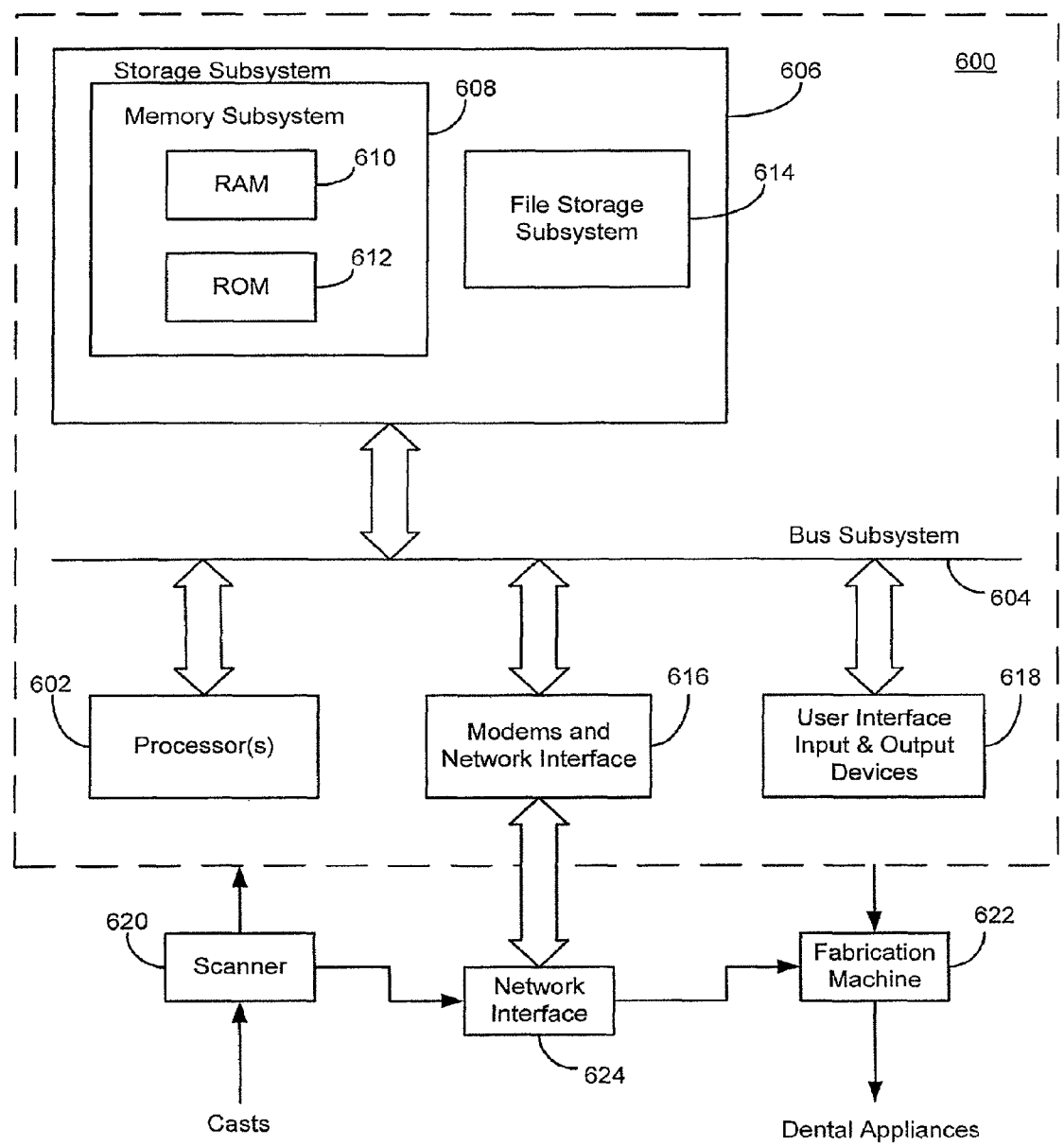
FIG. 10 is a diagram illustrating a computer system to support the fabrication of appliances.

Once the intermediate and final data sets have been created, the appliances may be fabricated as illustrated in FIG. 10. Common fabrication methods employ a rapid prototyping device 501 such as a stereolithography machine. A particularly suitable rapid prototyping machine is Model SLA-250/50 available from 3D System, Valencia, Calif. The rapid prototyping machine 501 selectively hardens a liquid or other non-hardened resin into a three-dimensional structure that can be separated from the remaining non-hardened resin, washed, and used either directly as the appliance or indirectly as a mold for producing the appliance. The prototyping machine 501 receives the individual digital data sets and produces one structure corresponding to each of the desired appliances. Generally, because the rapid prototyping machine 501 may utilize a resin having non-optimum mechanical properties and which may not be generally acceptable for patient use, the prototyping machine typically is used to produce molds which are, in effect, positive tooth models of each successive stage of the treatment. After the positive models are prepared, a conventional pressure or vacuum molding machine 551 is used to produce the appliances from a more suitable material, such as 0.03 inch thermal forming dental material, available from Tru-Tain Plastics, Rochester, Minn. 55902. Suitable pressure molding equipment is available under the trade name BIOSTAR from Great Lakes Orthodontics, Ltd., Tonawanda, N.Y. 14150. The molding machine 551 produces each of the appliances directly from the positive tooth model and the desired material. Suitable vacuum molding machines are available from Raintree Essix, Inc.

After production, the appliances can be supplied to the treating professional all at one time. The appliances are marked in some manner, typically by sequential numbering directly on the appliances or on tags, pouches, or other items which are affixed to or which enclose each appliance, to indicate their order of use. Optionally, written instructions may accompany the system which set forth that the patient is to wear the individual appliances in the order marked on the appliances or elsewhere in the packaging. Use of the appliances in such a manner will reposition the patient's teeth progressively toward the final tooth arrangement.

Because a patient's teeth may respond differently than originally expected, the treating clinician may wish to evaluate the patient's progress during the course of treatment. The system can also do this automatically, starting from the newly-measured in-course dentition. If the patient's teeth do not progress as planned, the clinician can revise the treatment plan as necessary to bring the patient's treatment back on course or to design an alternative treatment plan. The clinician may provide comments, oral or written, for use in revising the treatment plan. The clinician also can form another set of plaster castings of the patient's teeth for digital imaging and manipulation. The clinician may wish to limit initial aligner production to only a few aligners, delaying production on subsequent aligners until the patient's progress has been evaluated.

FIG. 11 is a simplified block diagram of a data processing system 600 that may be used to develop orthodontic treatment plans. The data processing system 600 typically includes at least one processor 602 that communicates with a number of peripheral devices via bus subsystem 604. These peripheral devices typically include a storage subsystem 606 (memory subsystem 608 and file storage subsystem 614), a set of user interface input and output devices 618, and an interface to outside networks 616, including the public switched telephone network. This interface is shown schematically as "Modems and Network Interface" block 616, and is coupled to corresponding interface devices in other data processing systems via communication network interface 624. Data processing system 600 could be a terminal or a low-end personal computer or a high-end personal computer, workstation or mainframe.

The user interface input devices typically include a keyboard and may further include a pointing device and a scanner. The pointing device may be an indirect pointing device such as a mouse, trackball, touchpad, or graphics tablet, or a direct pointing device such as a touchscreen incorporated into the display, or a three dimensional pointing device, such as the gyroscopic pointing device described in U.S. Pat. No. 5,440,326, other types of user interface input devices, such as voice recognition systems, can also be used. User interface output devices typically include a printer and a display subsystem, which includes a display controller and a display device coupled to the controller. The display device may be a cathode ray tube (CRT), a flat-panel device such as a liquid crystal display (LCD), or a projection device. The display subsystem may also provide non-visual display such as audio output.

Storage subsystem 606 maintains the basic required programming and data constructs. The program modules discussed above are typically stored in storage subsystem 606. Storage subsystem 606 typically comprises memory subsystem 308 and file storage subsystem 614.

Memory subsystem 608 typically includes a number of memories including a main random access memory (RAM) 610 for storage of instructions and data during program execution and a read only memory (ROM) 612 in which fixed instructions are stored. In the case of Macintosh-compatible personal computers the ROM would include portions of the operating system; in the case of IBM-compatible personal computers, this would include the BIOS (basic input/output system).

File storage subsystem 614 provides persistent (non-volatile) storage for program and data files, and typically includes at least one hard disk drive and at least one floppy disk drive (with associated removable media). There may also be other devices such as a CD-ROM drive and optical drives (all with their associated removable media). Additionally, the system may include drives of the type with removable media cartridges. The removable media cartridges may, for example be hard disk cartridges, such as those marketed by Syquest and others, and flexible disk cartridges, such as those marketed by 'omega. One or more of the drives may be located at a remote location, such as in a server on a local area network or at a site on the Internet's World Wide Web.

In this context, the term "bus subsystem" is used generically so as to include any mechanism for letting the various components and subsystems communicate with each other as intended. With the exception of the input devices and the display, the other components need not be at the same physical location. Thus, for example, portions of the file storage system could be connected via various local-area or wide-area network media, including telephone lines. Similarly, the input devices and display need not be at the same location as the processor, although it is anticipated that personal computers and workstations typically will be used.

Bus subsystem 604 is shown schematically as a single bus, but a typical system has a number of buses such as a local bus and one or more expansion buses (e.g., ADB, SCSI, ISA, EISA, MCA, NuBus, or PCI), as well as serial and parallel ports. Network connections are usually established through a device such as a network adapter on one of these expansion buses or a modem on a serial port. The client computer may be a desktop system or a portable system.

Scanner 620 is responsible for scanning casts of the patient's teeth obtained either from the patient or from an orthodontist and providing the scanned digital data set information to data processing system 600 for further processing. In a distributed environment, scanner 620 may be located at a remote location and communicate scanned digital data set information to data processing system 600 via network interface 624. Fabrication machine 622 fabricates dental appliances based on intermediate and final data set information received from data processing system 600. In a distributed environment, fabrication machine 622 may be located at a remote location and receive data set information from data processing system 600 via network interface 624.

The invention has been described in terms of particular embodiments. Other embodiments are within the scope of the following claims. For example, the three-dimensional scanning techniques described above may be used to analyze material characteristics, such as shrinkage and expansion, of the materials that form the tooth castings and the aligners. Also, the 3D tooth models and the graphical interface described above may be used to assist clinicians that treat patients with conventional braces or other conventional orthodontic appliances, in which case the constraints applied to tooth movement would be modified accordingly.

What is claimed is:

1. A method for dental treatment planning, comprising:
    receiving, by one or more computers, a set of diagnostic data comprising one or more malocclusions and a current arrangement of a patient's teeth;
    prior to determining an initial desired arrangement of the patient's teeth, executing, by the one or more computers, a first evaluation routine for the set of diagnostic data comprising validating the set of diagnostic data at least against one or more case selection criteria for a desired treatment system, wherein successful validation indicates that the patient's teeth are acceptable for treatment using the desired treatment system;
    determining the initial desired arrangement of the patient's teeth;
    after successful validation by the first evaluation routine and determination of the initial desired arrangement, executing, by the one or more computers, a second evaluation routine that evaluates the distance the teeth move between the current arrangement and the initial desired arrangement against a magnitude of movement included in the one or more case selection criteria, wherein the magnitude of movement being less than a maximum permitted for treatment using the desired treatment system indicates that the second evaluation routine is successful and the treatment system may be utilized for treatment of the patient;

after successful evaluation by the second evaluation routine, generating, by the one or more computers, a treatment plan for moving the patient's teeth from the current arrangement toward the initial desired arrangement of the patient's teeth using the desired treatment system, the treatment plan formulated using the set of diagnostic data according to parameters of the desired treatment system, wherein the treatment plan includes data sets corresponding to the shape of a plurality of appliances;

outputting the data sets corresponding to the shape of the plurality of appliances for treating the patients to a fabrication machine; and controlling, by the one or more computers, the fabrication machine to produce the plurality of appliances for treating the patient according to the outputted data sets.

2. The method of claim 1, wherein the set of diagnostic data is indicative of at least one of: (a) which teeth are present, (b) condition of the teeth, (c) position of the teeth in a respective dental arch, (d) relationship of at least one tooth to other teeth, (e) size of the teeth, or (f) alignment of the teeth.

3. The method of claim 1, wherein the first evaluation routine further comprises detecting whether there is conflicting data in the set of diagnostic data.

4. The method of claim 3, wherein the set of diagnostic data comprises data of the patient's teeth from a plurality of views, and wherein the first evaluation routine comprises matching data of the patient's teeth from a first view of the plurality of views to data of the patient's teeth from a second view of the plurality of views.

5. The method of claim 3, further comprising generating feedback information if conflicting data is detected in the set of diagnostic data.

6. A computer system for dental treatment planning, comprising:
one or more processors; and
memory, including instructions executable by the one or more processors to cause the computer system to at least:
receive a set of diagnostic data comprising one or more malocclusions and a current arrangement of a patient's teeth;
prior to determining an initial desired arrangement of the patient's teeth, execute a first evaluation routine for the set of diagnostic data comprising validating the set of diagnostic data against at least against one or more case selection criteria for a desired treatment system, wherein successful validation indicates that the patient's teeth are acceptable for treatment using the desired treatment system;
determining the initial desired arrangement of the patient's teeth;
after successful validation by the first evaluation routine and determination of the initial desired arrangement, executing, by the one or more processors, a second evaluation routine that evaluates the distance the teeth move between the current arrangement and the initial desired arrangement against a maximum magnitude of movement included in the one or more case selection criteria, thereby validating that a magnitude of the movement is less than a maximum permitted for treatment using the desired treatment system;

after successful evaluation by the second evaluation routine, generate a treatment plan for moving the patient's teeth from the current arrangement toward the initial desired arrangement of the patient's teeth using the desired treatment system, the treatment plan formulated using the set of diagnostic data according to parameters of the desired treatment system, wherein the treatment plan includes data sets corresponding to the shape of a plurality of appliances; and output the data sets corresponding to the shape of the plurality of appliances for treating the patients to a fabrication machine; and controlling, by the one or more computers, the fabrication machine to produce the plurality of appliances for treating the patient according to the outputted data sets.

7. The system of claim 6, wherein the instructions further cause the computer system to:
generate a first set of questions relating to a treatment goal for the patient's teeth;
receive, in response to the first set of questions, a set of treatment goal data relating to a desired arrangement of the patient's teeth; and
execute a third evaluation routine for the set of treatment goal data comprising validating the set of treatment goal data against at least one of the set of diagnostic data or one or more case selection criteria for the desired treatment system, thereby determining feasibility of the treatment goal.

8. The system of claim 7, wherein the first set of questions are generated based on the set of diagnostic input data.

9. The system of claim 7, wherein the instructions further cause the computer system to:
generate a second set of questions relating to a desired treatment path for the patient's teeth;
receive, in response to the second set of questions, a set of treatment path data relating to a desired treatment path for moving the patient's teeth toward the desired arrangement; and
execute a fourth evaluation routine for the set of treatment path data comprising validating the set of treatment path data against at least one of the set of diagnostic data, the set of treatment goal data, or the one or more case selection criteria for the desired treatment system, thereby determining feasibility of the desired treatment path.

10. A computer system for dental treatment planning, comprising:
one or more processors; and
memory, including instructions executable by the one or more processors to cause the computer system to at least:
receive a set of diagnostic data comprising one or more malocclusions and a current arrangement of a patient's teeth;
prior to determining an initial desired arrangement of the patient's teeth, execute a first evaluation routine for the set of diagnostic data comprising validating the set of diagnostic data so as to detect whether there is any conflicting data in the set of the diagnostic data and wherein successful validation indicates the patient's teeth are acceptable for treatment using a desired treatment system;

determine an initial desired arrangement of the patient's teeth;

after successful validation by the first evaluation routine and determination of the initial desired arrangement, execute a second evaluation routine that evaluates the distance the teeth move between the current arrangement and the initial desired arrangement, thereby validating that a magnitude of the movement is less than a maximum permitted for treatment using the desired treatment system;

after successful validation by the second evaluation routine generate a treatment plan for moving the patient's teeth from the current arrangement toward the initial desired arrangement of the patient's teeth using the desired treatment system, the treatment plan formulated using the set of diagnostic data according to parameters of the desired treatment system, wherein the treatment plan includes data sets corresponding to the shape of a plurality of appliances;

the data sets corresponding to the shape of the plurality of appliances for treating the patients to a fabrication machine; and controlling, by the one or more computers, the fabrication machine to produce the plurality of appliances for treating the patient according to the outputted data sets.

11. The system of claim 10, wherein the treatment plan comprises a plurality of treatment stages.

12. The system of claim 11, wherein the instructions further cause the computer system to generate data for fabricating one or more dental appliances to move the patient's teeth from at least one treatment stage of the plurality of treatment stages to another treatment stage of the plurality of treatment stages.

13. The system of claim 12, wherein the instructions further cause the computer to:

generate one or more questions regarding timing of delivery of the one or more dental appliances; and receive one or more responses to the one or more questions.

14. The system of claim 12, wherein the instructions further cause the computer to:

execute a third evaluation routine for the treatment plan comprising validating the treatment plan against one or more properties of the one or more dental appliances.

* * * * *